United States Patent [19]
Houghton et al.

[11] Patent Number: 5,706,950
[45] Date of Patent: Jan. 13, 1998

[54] DISPOSABLE DIAPER CHANGING PACK

[75] Inventors: Dawn Lynn Ilnicki Houghton; Jean Sandra Feyen, both of Appleton; Wilfred Eugene Riddell, Neenah; Paula Cardinahl Winkel, Chilton; Joseph Eric Winter, Appleton, all of Wis.

[73] Assignee: Kimberly-Clark Worldwide, Inc., Neenah, Wis.

[21] Appl. No.: 657,734

[22] Filed: May 31, 1996

[51] Int. Cl.⁶ .................. B65D 85/00; A61L 15/16
[52] U.S. Cl. .............. 206/581; 206/440; 604/385.1
[58] Field of Search ............... 428/35.7, 36.1, 428/68, 76, 130, 190, 193; 206/494, 440, 581, 811, 812, 823, 223, 438; 604/385.1

[56] References Cited

U.S. PATENT DOCUMENTS

| H1454 | 6/1995 | Cucuzza et al. | 604/385.1 |
|---|---|---|---|
| D. 204,737 | 5/1966 | Draheim . | |
| D. 266,470 | 10/1982 | Gammons et al. . | |
| D. 270,983 | 10/1983 | Gammons et al. . | |
| D. 290,908 | 7/1987 | Thomas . | |
| D. 294,909 | 3/1988 | Donnor . | |
| D. 324,567 | 3/1992 | Leslie et al. . | |
| D. 334,426 | 3/1993 | Meis | D24/126 |
| D. 341,027 | 11/1993 | Godden et al. . | |
| D. 343,233 | 1/1994 | Lanmon et al. | D24/126 |
| D. 366,315 | 1/1996 | Oranday | D24/126 |
| D. 366,368 | 1/1996 | McCarthy | D6/333 |
| 2,955,331 | 10/1960 | Nelson | 206/440 |
| 3,117,607 | 1/1964 | Siegel . | |
| 3,369,545 | 2/1968 | Wanberg . | |
| 3,489,194 | 1/1970 | Hoover . | |

(List continued on next page.)

FOREIGN PATENT DOCUMENTS

| 29393 | 12/1985 | Australia . |
|---|---|---|
| 0023417 | 2/1981 | European Pat. Off. . |
| 0078267 | 5/1983 | European Pat. Off. . |
| 0121966 | 10/1984 | European Pat. Off. . |
| 0213241 | 3/1987 | European Pat. Off. . |
| 0218568 | 4/1987 | European Pat. Off. . |
| 2399824 | 3/1979 | France . |
| 2478972 | 10/1981 | France . |
| 2699391 | 6/1994 | France . |
| 2715549 | 8/1995 | France . |
| 2238286 | 5/1991 | United Kingdom . |
| 227120 | 4/1994 | United Kingdom . |
| 8810219 | 12/1988 | WIPO . |
| 9116871 | 11/1991 | WIPO . |
| 9405500 | 3/1994 | WIPO . |
| 9410953 | 5/1994 | WIPO . |
| 9410954 | 5/1994 | WIPO . |
| 9410955 | 5/1994 | WIPO . |
| 9410956 | 5/1994 | WIPO . |
| 9410957 | 5/1994 | WIPO . |

*Primary Examiner*—Jimmy G. Foster
*Attorney, Agent, or Firm*—Paul Yee

[57] ABSTRACT

A distinctive composite article has a longitudinal, length dimension and a lateral, width dimension. The article includes a flexible outer shell portion having a shell length and a shell width. At least a portion of a flexible drape layer is substantially affixed to the shell portion, and the drape layer has a drape width which is larger than the shell width. Additionally, the drape layer may have a drape length which is larger than the shell length. The drape layer includes a first laterally extending fold line, a first longitudinally extending fold line and at least a second longitudinally extending fold line. The longitudinally extending fold lines provide for a laterally-folded drape width which is not more than the shell width. The drape layer may also include at least a second laterally extending fold line, and the laterally extending fold lines may also provide for a longitudinally-folded drape length which is not more than the shell length. At least one removable, unit component is contained and enveloped within the drape portion when the drape portion is folded. A closure mechanism holds the shell portion in a closed-package condition which substantially envelops the drape portion when the drape portion is folded. An article opening means can selectively defeat the closure means to provide access to the unit component.

20 Claims, 20 Drawing Sheets

U.S. PATENT DOCUMENTS

| | | | |
|---|---|---|---|
| 3,585,999 | 6/1971 | Wanberg . | |
| 3,731,689 | 5/1973 | Schaar . | |
| 3,837,955 | 9/1974 | Schaar . | |
| 3,877,432 | 4/1975 | Gellert . | |
| 3,920,019 | 11/1975 | Schaar . | |
| 3,927,674 | 12/1975 | Schaar . | |
| 3,963,029 | 6/1976 | Brooks . | |
| 4,154,323 | 5/1979 | Sneider . | |
| 4,221,221 | 9/1980 | Ehrlich . | |
| 4,417,894 | 11/1983 | Norris . | |
| 4,430,087 | 2/1984 | Azpiri . | |
| 4,493,713 | 1/1985 | Izzo . | |
| 4,522,381 | 6/1985 | Ludwick . | |
| 4,556,146 | 12/1985 | Swanson et al. | 206/440 |
| 4,566,130 | 1/1986 | Coates | 383/15 |
| 4,597,121 | 7/1986 | Bouma . | |
| 4,604,096 | 8/1986 | Dean et al. . | |
| 4,650,481 | 3/1987 | O'Connor et al. . | |
| 4,702,378 | 10/1987 | Finkel | 206/581 |
| 4,712,258 | 12/1987 | Eves . | |
| 4,723,300 | 2/1988 | Aranow | 383/4 |
| 4,735,316 | 4/1988 | Froidh | 206/438 |
| 4,738,678 | 4/1988 | Paulis . | |
| 4,743,240 | 5/1988 | Powell . | |
| 4,753,657 | 6/1988 | Curtis . | |
| 4,781,277 | 11/1988 | Lim . | |
| 4,781,712 | 11/1988 | Barabino et al. | 604/385.1 |
| 4,788,726 | 12/1988 | Rafalko . | |
| 4,788,733 | 12/1988 | Lerner . | |
| 4,790,840 | 12/1988 | Cortina | 604/385.1 |
| 4,792,024 | 12/1988 | Morton et al. . | |
| 4,808,175 | 2/1989 | Hansen | 604/385.1 |
| 4,834,737 | 5/1989 | Khan | 604/385.2 |
| 4,857,066 | 8/1989 | Allison | 604/385.1 |
| 4,886,150 | 12/1989 | Fitzsimmons . | |
| 4,886,697 | 12/1989 | Perdelwitz, Jr. et al. . | |
| 4,900,377 | 2/1990 | Redford et al. . | |
| 4,902,283 | 2/1990 | Rojko et al. | 604/290 |
| 4,917,505 | 4/1990 | Bullard et al. | 383/4 |
| 4,917,693 | 4/1990 | Terry | 604/385.1 |
| 4,923,455 | 5/1990 | Dean et al. | 604/385.1 |
| 4,931,052 | 6/1990 | Feldman | 604/385.1 |
| 4,939,017 | 7/1990 | Foxman . | |
| 4,961,522 | 10/1990 | Weber . | |
| 4,963,140 | 10/1990 | Robertson et al. | 604/389 |
| 4,964,859 | 10/1990 | Feldman | 604/385.1 |
| 4,968,311 | 11/1990 | Chickering et al. | 604/385.1 |
| 4,968,312 | 11/1990 | Khan | 604/385.1 |
| 4,972,532 | 11/1990 | Juan . | |
| 4,999,863 | 3/1991 | Kane . | |
| 5,010,610 | 4/1991 | Ackley . | |
| 5,016,778 | 5/1991 | Reiland et al. . | |
| 5,037,414 | 8/1991 | Booth | 604/385.1 |
| 5,062,557 | 11/1991 | Mahvi . | |
| 5,071,414 | 12/1991 | Elliot | 604/385.1 |
| 5,088,139 | 2/1992 | Bloom . | |
| 5,133,085 | 7/1992 | de Pasquale Amicarelli et al. . | |
| 5,141,505 | 8/1992 | Barrett | 604/385.1 |
| 5,171,671 | 12/1992 | Roessler et al. | 604/391 |
| 5,182,828 | 2/1993 | Alivizatos . | |
| 5,192,606 | 3/1993 | Proxmire et al. . | |
| 5,207,508 | 5/1993 | Koutsis, Jr. | 383/4 |
| 5,230,450 | 7/1993 | Mahvi et al. . | |
| 5,234,143 | 8/1993 | Mahvi et al. . | |
| 5,242,057 | 9/1993 | Cook et al. | 206/581 |
| 5,252,374 | 10/1993 | Larsonneur . | |
| 5,255,817 | 10/1993 | Reiland et al. . | |
| 5,261,531 | 11/1993 | Nieves | 206/205 |
| 5,279,604 | 1/1994 | Robertson et al. | 604/389 |
| 5,290,268 | 3/1994 | Oliver et al. | 604/359 |
| 5,295,988 | 3/1994 | Muckenfuhs et al. | 604/385.2 |
| 5,304,158 | 4/1994 | Webb | 604/385.1 |
| 5,318,107 | 6/1994 | Bell . | |
| 5,326,300 | 7/1994 | Sonders | 446/74 |
| 5,350,067 | 9/1994 | Beltran | 206/440 |
| 5,413,568 | 5/1995 | Roach et al. | 604/358 |
| 5,439,154 | 8/1995 | Delligatti . | |
| 5,439,405 | 8/1995 | Storey et al. | 441/127 |
| 5,443,161 | 8/1995 | Jonese | 206/581 |
| 5,462,166 | 10/1995 | Minton et al. | 206/440 |
| 5,484,636 | 1/1996 | Berg et al. | 206/581 |
| 5,569,228 | 10/1996 | Byrd et al. | 206/438 |
| 5,569,230 | 10/1996 | Fischer et al. | 206/438 |

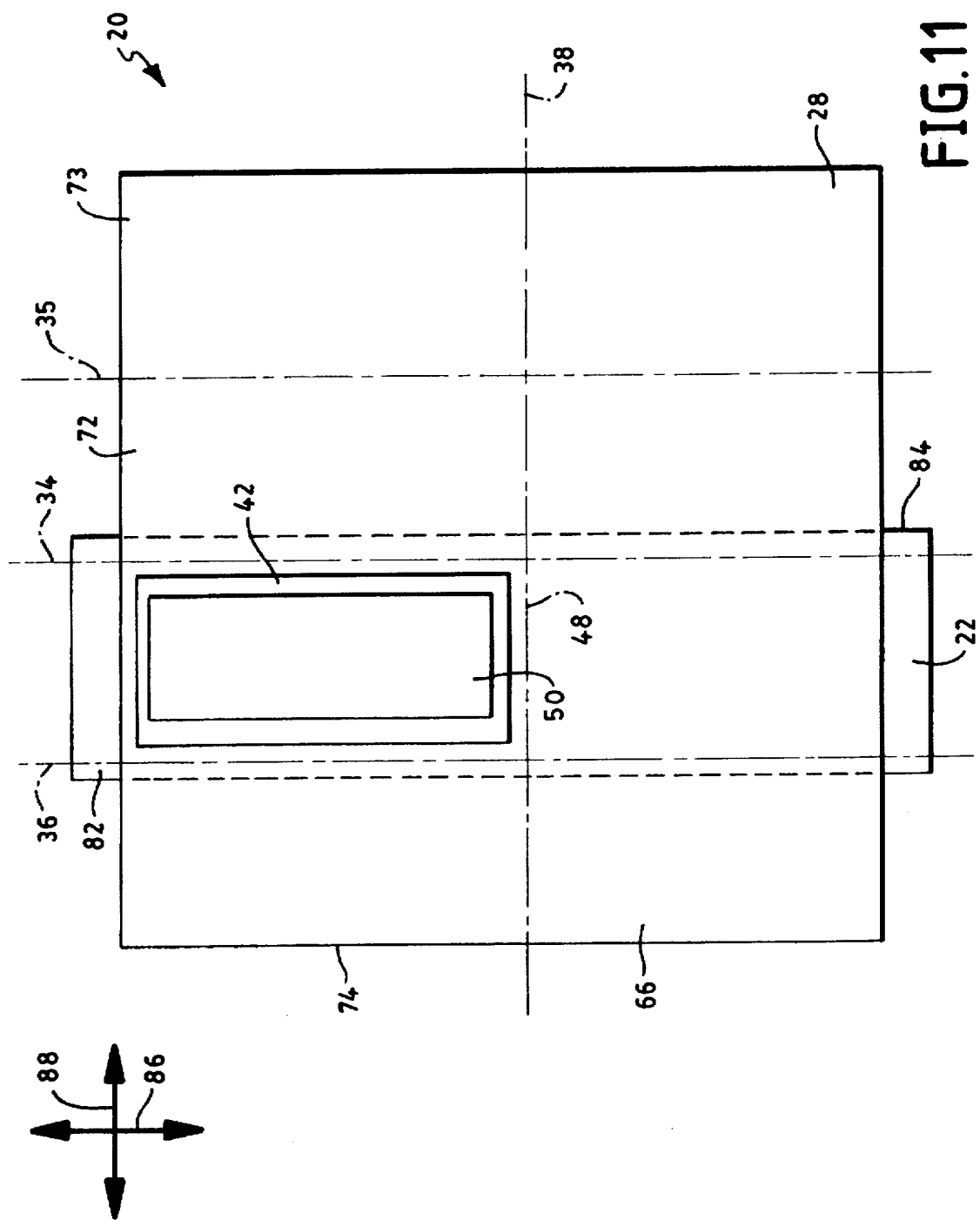

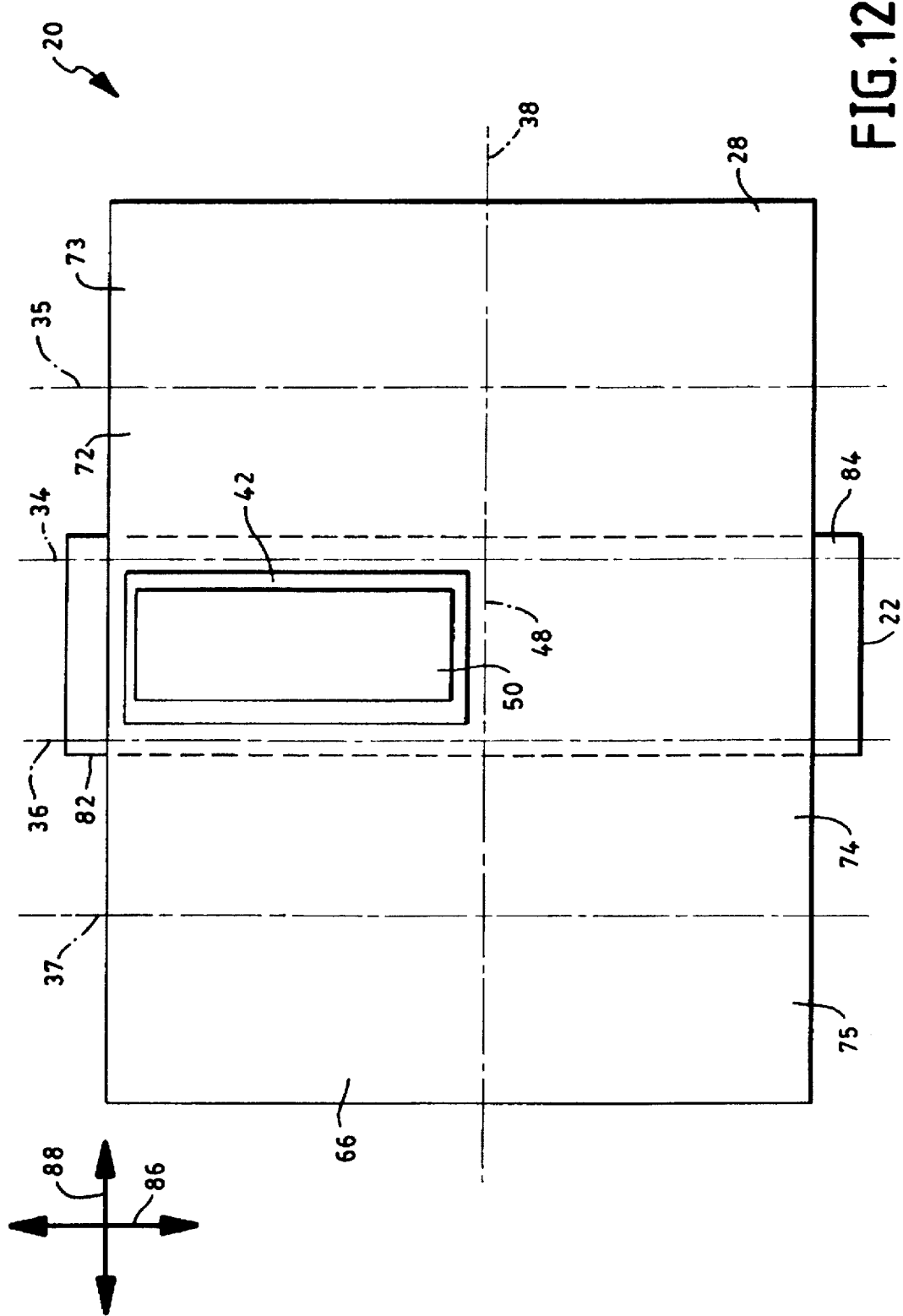

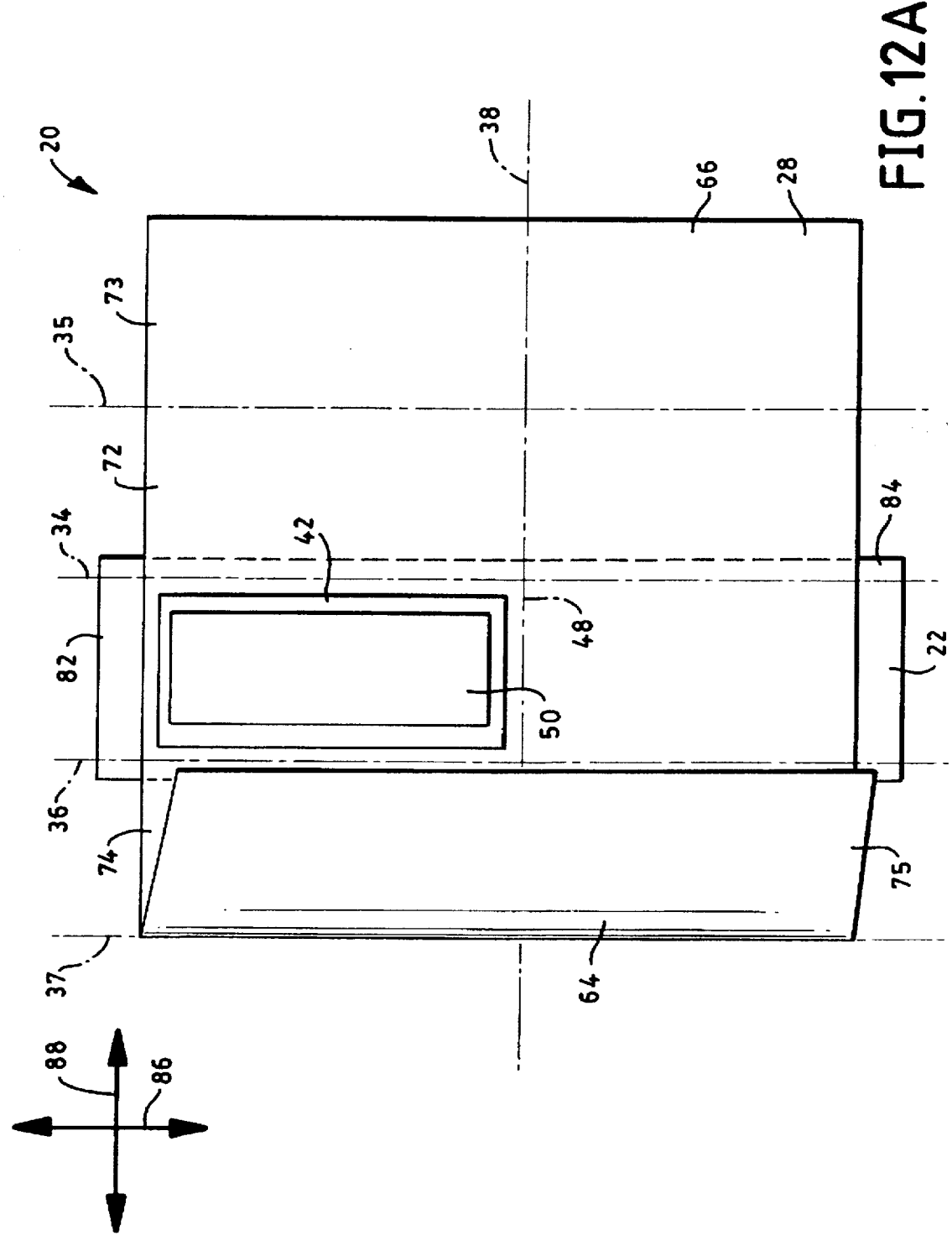

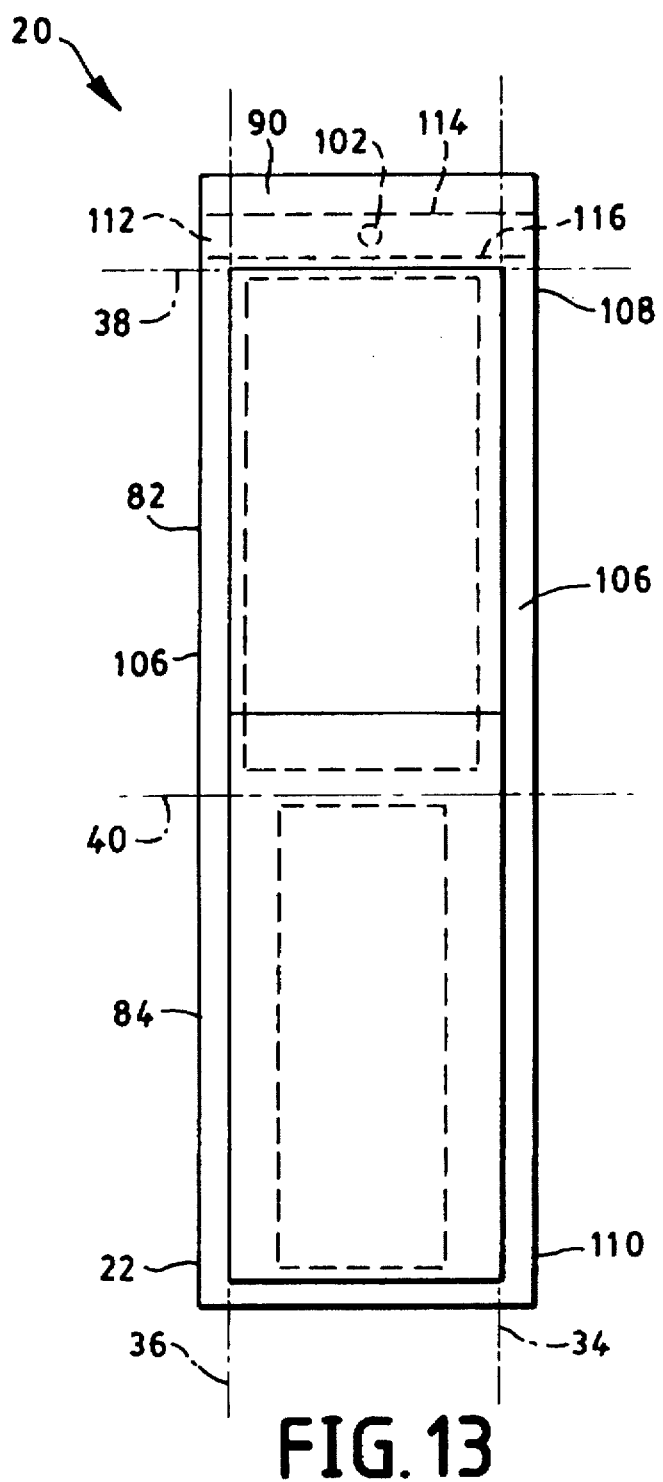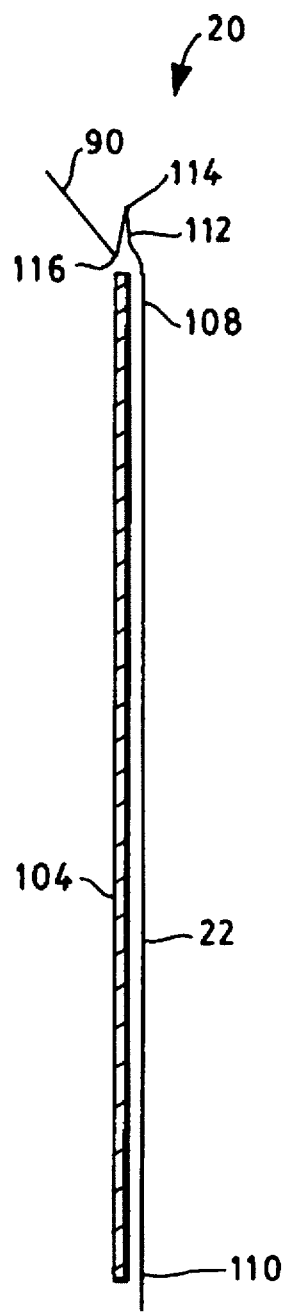
FIG. 13
FIG. 13A

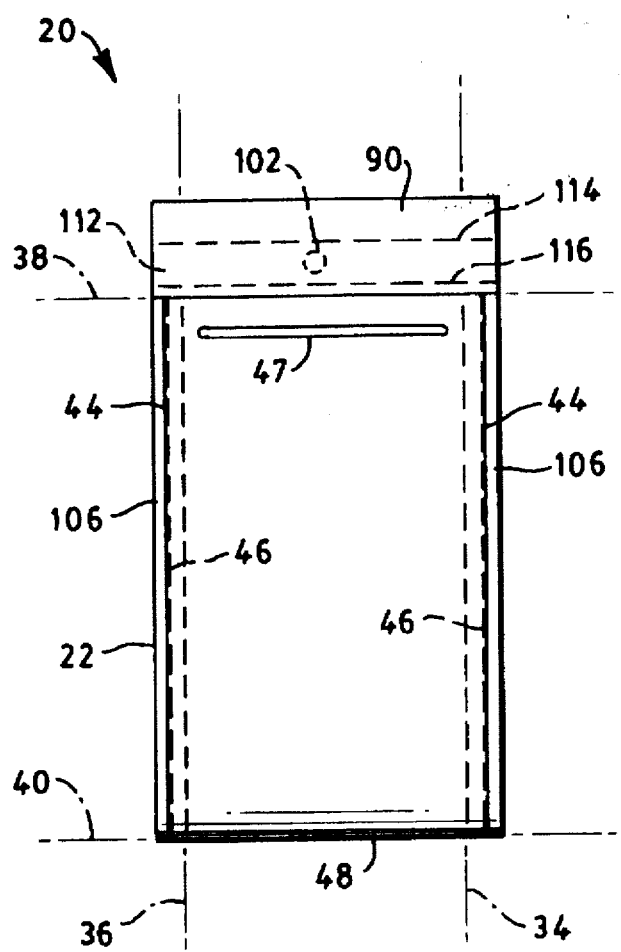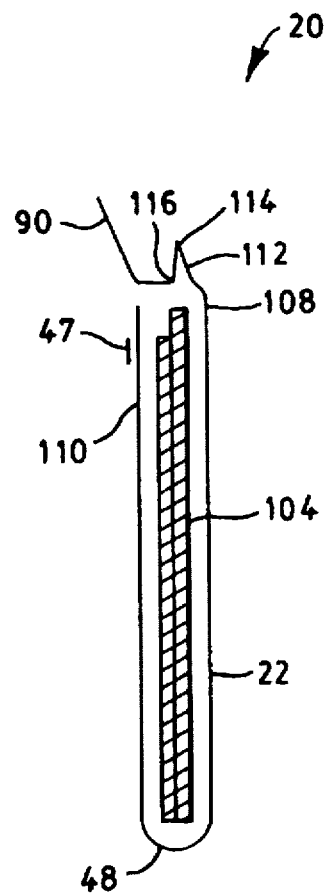
FIG. 14
FIG. 14A

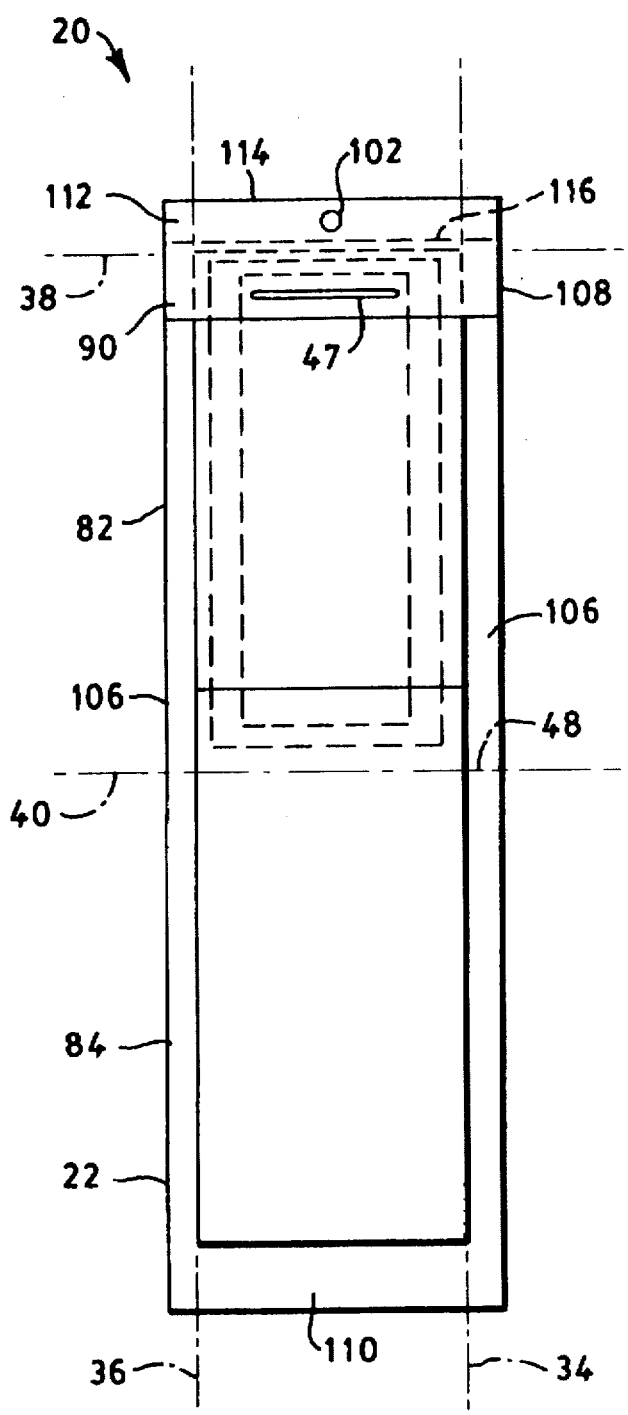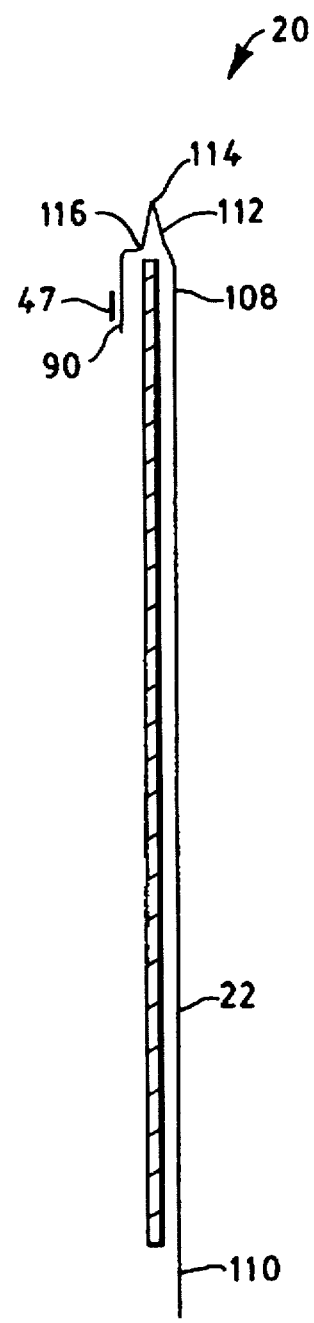
FIG. 16
FIG. 16A

5,706,950

DISPOSABLE DIAPER CHANGING PACK

FIELD OF THE INVENTION

The present invention relates to a composite article for providing a desired combination of related and cooperating components for maintenance or cleaning operations. More particularly, the invention relates to a composite article for providing a related combination of components for the hygiene of an individual, such as the changing of a diaper on an infant.

BACKGROUND OF THE INVENTION

Conventional systems for providing hygienic components for the care of an individual have included infant care bags for storing bottles, diapers, wet wipes, and other infant care supplies. Particular diaper changing bags have included closeable storage compartments, and have included carrying handles and foldable flaps.

Other systems have provided a package which included a disposable diaper, a separate changing pad and disposal container. The package could also include a closeable packet for retaining a moistened towelette. Still other systems have included a disposable diaper with a diaper body having a pouch arranged to enclose a changing pad. The changing pad is removable from the pouch, and containers for holding personal care products, such as lotions, powders, oils, ointments, and wipes, are connected to the changing pad.

Conventional systems, such as those described above, have been cumbersome and unwieldy. Where components have been packaged together, it has been difficult to deploy the changing pad without scattering the other package contents. Where components such as changing pads and moistened towelettes are contained within the structure of a disposable diaper, the infant may be burdened with carrying about extra items which are bulky or uncomfortable. When components have been removed from a pouch section of the diaper, the diaper has been left unsightly and with loose openings. Where a changing pad is small enough to be folded and contained within a pouch section of a diaper, the changing pad may be too small, may be too cumbersome to unfold, and may provide inadequate coverage of the appointed changing area. If a bag or package is employed to contain a disposable diaper, changing pad, and moistened towelettes, it has been difficult to simultaneously manage the bag contents and a squirming infant. In addition, needed items may have been forgotten when the bag was initially packed.

As a result, there has remained a need for a composite article which conveniently and efficiently provides a desired combination of a large-area drape or pad along with one or more other, individual associated items. In particular, there has remained a need for a convenient and easy to use composite article which includes needed components for individual hygiene. For example, there has remained a need for a composite article which provides a large-area changing pad and an individual disposable garment, along with an optional prepackaged quantity of pre-moistened towelettes or wet wipes.

BRIEF DESCRIPTION OF THE INVENTION

Generally stated, the present invention provides a distinctive composite article having a longitudinal, length dimension and a lateral, width dimension. The article includes a flexible outer shell portion having a shell length and a shell width. At least a portion of a flexible drape layer is substantially affixed to the shell portion, and the drape layer has a drape width which is larger than the shell width. The drape layer includes a first laterally extending fold line, a first longitudinally extending fold line and at least a second longitudinally extending fold line. The longitudinally extending fold lines provide for a laterally-folded drape width which is not more than the shell width. At least one removable, unit component is contained and enveloped within the drape portion when the drape portion is folded. A closure mechanism holds the shell portion in a closed-package condition which substantially envelops the drape portion when the drape portion is folded. An article opening means can selectively defeat the closure means to provide access to the unit component.

In particular aspects, the composite article can include a drape layer having a drape length which is larger than the shell length, and at least a second laterally extending fold line, with the laterally extending fold lines providing for a longitudinally-folded drape length which is not more than the shell length. In other aspects, the composite article can include a drape layer which is at least partially superposed, and desirably, is substantially totally superposed onto said outer shell portion.

When compared to conventional devices, such as those described above, the various aspects of the composite article of the invention can provide a more effective combination and presentation of associated and interrelated components. In particular, aspects the present invention can more efficiently provide a more readily usable and effective combination of personal hygiene components, such as large-area changing pad, a disposable diaper, and a plurality of wet wipes. The composite article advantageously provides an ergonomically designed combination package which is more easily opened and manipulated. The drape layer can be easily deployed while the other contained components are maintained in place. Once the drape layer is opened, the other components are conveniently presented for ready use.

BRIEF DESCRIPTION OF THE DRAWINGS

The present invention will be more fully understood and further advantages will become apparent when reference is made to the following detailed description of the invention and the drawings, in which:

FIG. 11 representatively shows an article of the invention having a single lateral fold line, multiple longitudinal fold lines and an asymmetrically located outer shell member;

FIG. 12 representatively shows another article of the invention having a single lateral fold line and a plurality of longitudinal fold lines;

FIG. 12A representatively shows an article of FIG. 12 in a partially folded and partially closed condition;

FIG. 13 representatively shows an article of the invention which has a reinforced end region and is in its partially folded and closed condition FIG. 13A representatively shows a simplified, schematic, cross-sectional view of the article of FIG. 13;

FIG. 14 representatively shows an article of FIG. 13 in a further folded and partially closed condition;

FIG. 14A representatively shows a simplified, schematic, cross-sectional view of the article of FIG. 14;

FIG. 16 representatively shows another article which has its closure flap moved to a closed position;

FIG. 16A representatively shows a simplified, schematic, cross-sectional view of the article of FIG. 16;

DETAILED DESCRIPTION OF THE INVENTION

The various embodiments of the invention will be described in the context of a composite article which includes a disposable absorbent garment article, such as a disposable diaper. Typically, the disposable articles are intended for limited use and are not intended to be laundered or otherwise cleaned for reuse. It is, however, readily apparent that the present invention could also be employed with other articles, such as children's training pants, adult incontinence products, feminine care products, items for automobile oil-changing kits, items for jewelry cleaning kits, items for medical kits, items for first-aid kits, items for gun cleaning kits, items for shoe polish kits, items for use at the beach, or the like.

Figure 1:
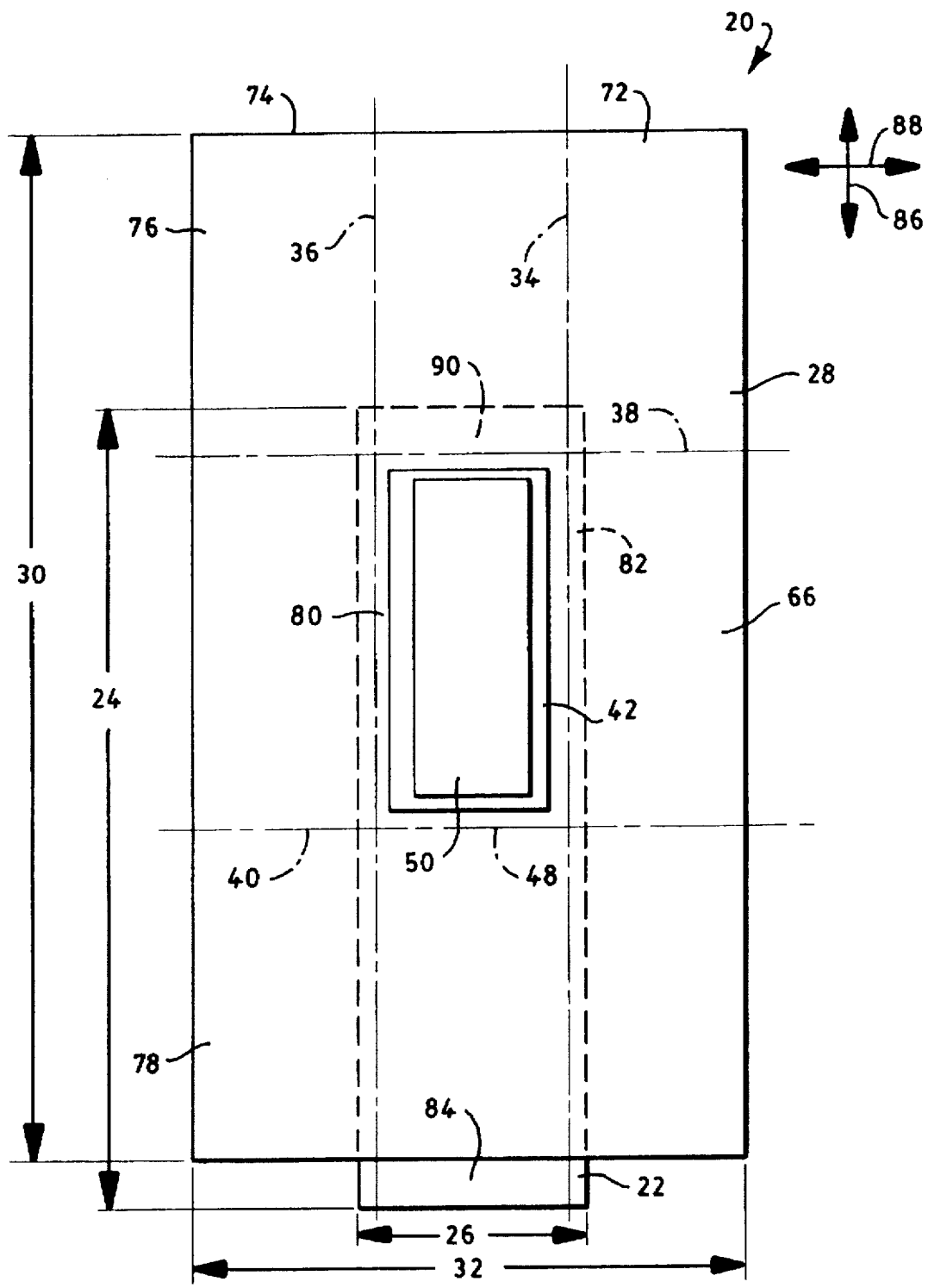
FIG. 1 representatively shows a composite article of the invention in a completely unfolded condition.
Figures 2, 2A:
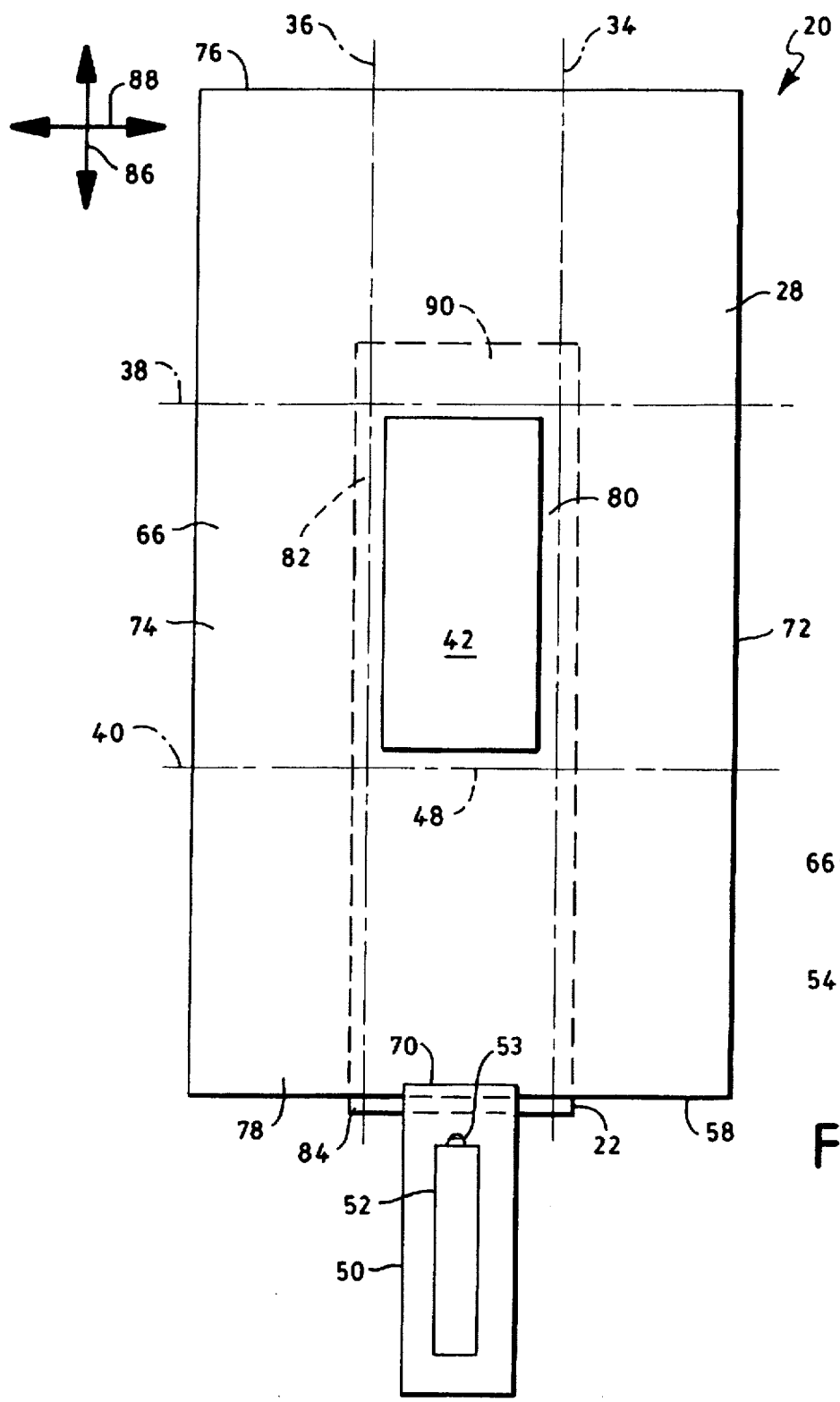
FIG. 2 representatively shows another composite article of the invention in an open, unfolded condition and arranged in an activated, working position.
FIG. 2A representatively shows an enlarged, partial cross-sectional view of a laminated drape layer.
Figure 7:
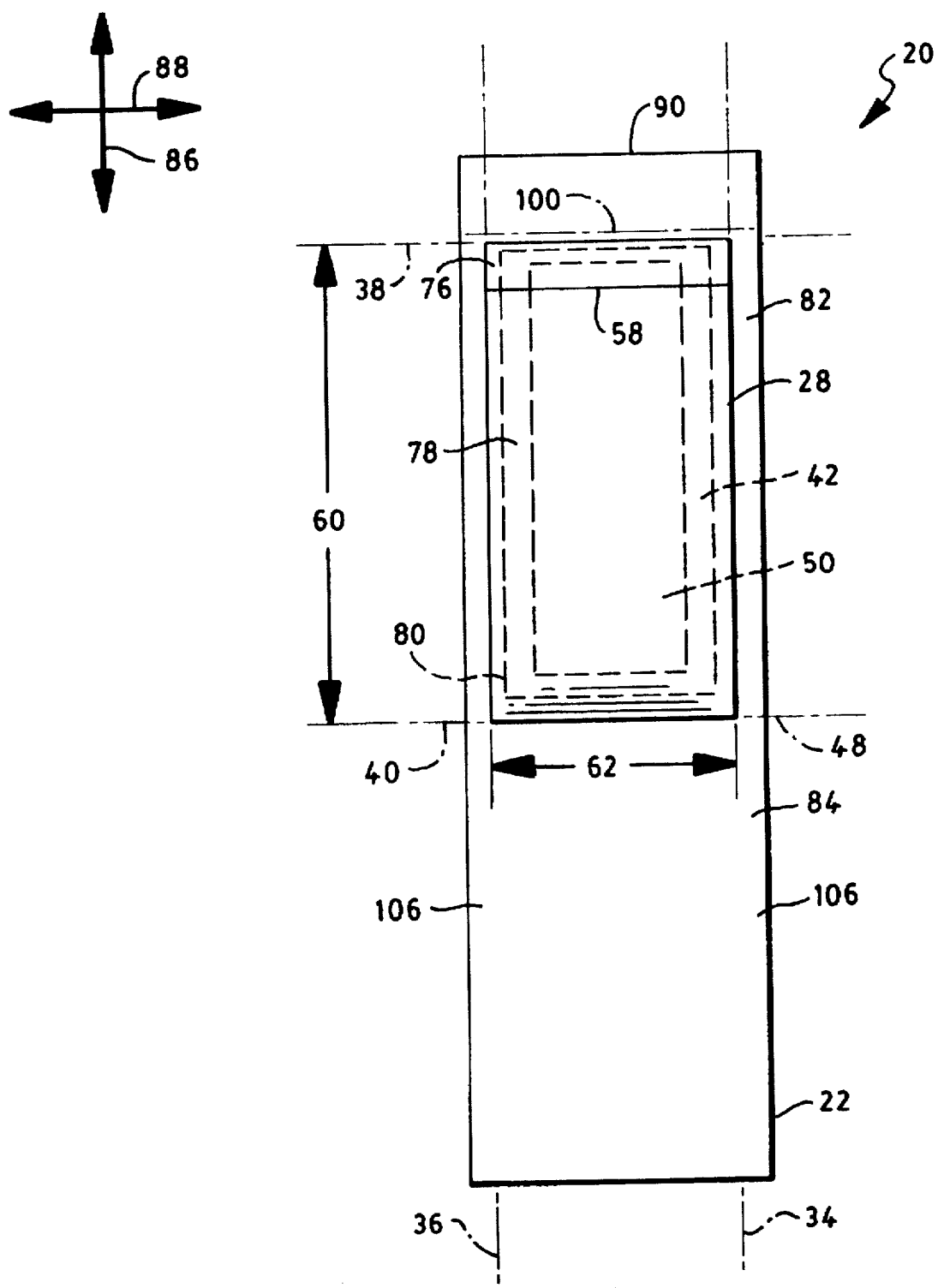
FIG. 7 representatively shows an article of FIG. 6 in a further folded condition with an open outer shell portion.
Figure 8:
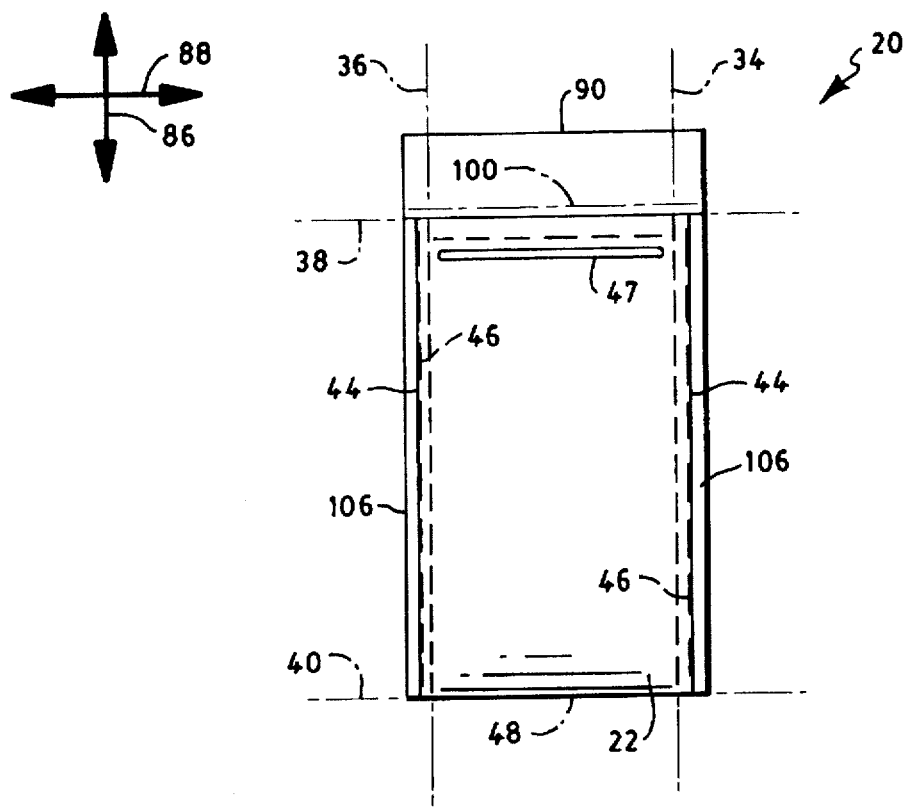
FIG. 8 representatively shows an article of FIG. 7 with a folded outer shell portion and an open closure flap.

With reference to FIGS. 1 and 2, a representative composite article 20 is generally shown in its fully open and completely unfolded condition. The composite article has a longitudinal length dimension 86 and a lateral width dimension 88, and includes a flexible outer shell member portion 22 having a shell length 24 and a shell width 26. At least a portion of a flexible drape layer 28 is affixed to the shell portion 22, and in the shown arrangement, is superposed over substantially the entire outer shell portion 22. The drape layer has an open drape width 32 which is larger than the open shell width 26, and includes an appointed first laterally extending fold line 38, an appointed first longitudinally extending fold line 34 and at least an appointed second longitudinally extending fold line 36. The longitudinally extending fold lines can provide for a laterally-folded drape width 62 (FIG. 7) which is not more than the shell width 26. At least one removable, unit component, such as a disposable diaper article 42 or other garment article, is contained and enveloped within the drape layer portion 28 when the drape layer portion is folded. With reference to FIG. 8, a closure means, such as a system of attachments 44, is configured to hold the shell portion 22 in a closed-package condition which can contain and substantially envelop the drape layer 28 when the drape layer is folded. An article opening means, such as a mechanism or system which includes frangible line regions 46, is configured to selectively defeat the closure means to provide access to the at least one unit component. The composite article 20 may additionally include an optional second unit component, such as provided by a packet 50.

In particular aspects, the composite article the drape layer may also have an open drape length 30 which is larger than the open shell length 24, and may include at least an appointed second laterally extending fold line 40. The laterally extending fold lines 38 and 40 can provide for a longitudinally-folded drape length 60 which is not more than, and desirably is less than, the outer shell length 24. In addition, the completely folded drape length 60 is not more than, and desirably is less than, a completely folded length 94 (FIG. 9) of the outer shell 22. In other aspects, the composite article can include a drape layer which is at least partially overlapped or otherwise partially superposed on the outer shell portion.

In particular arrangements, such as illustrated in FIG. 1, the packet can be located in a generally central section of the drape layer 28, along with the first unit component. In other arrangements, such as illustrated in FIG. 2, the packet 50 can be located adjacent a terminal edge of the drape layer, and can optionally be selectively pivotable from its storage position, which is substantially inboard of the terminal edge, to its active, working position, which is substantially outboard of the terminal edge. Still other configurations may include a displaying mechanism 102 (e.g. FIG. 15) for presenting the composite article to a potential user.

In the various configurations of the invention, the outer shell member 22 is desirably composed of any operable sheet material, which is sufficiently flexible and a foldable, such as a woven fabric, a nonwoven fabric, a cellulosic sheet, a polymer film or the like, as well as combinations thereof. The shell member may be a substantially unitary member composed of a single, unit sheet of material, or may be an assembly composed of a plurality of pieces joined and affixed along their edges to form a larger contiguous sheet. Suitable woven fabrics can include, for example, woven fabrics of cotton, rayon, linen, as well as other natural or synthetic fibers, and the like. Examples of suitable nonwoven fabrics include hydroentangled pulp, spunbond fabrics, SMS (spunbond-meltblown-spunbond) fabrics, SBL (stretch-bonded-laminate) fabrics, GORTEX fabrics, STL (stretch-thermal-laminate) fabrics or the like, as well as combinations thereof. Suitable polymer films include, for example, films composed of polyethylene, LDPE (low-density polyethylene), LLDPE (linear low-density polyethylene), ULDPE (ultra-low-density polyethylene), HDPE (high-density polyethylene), polypropylene, polyethylene/EVA (ethylene vinyl acetate) copolymers, a blend of polyethylenes, paper, nylon, cellophane, PVC (polyvinyl chloride) film, metallic foil, metalized films, polyester films, microporous breathable films or the like, as well as combinations thereof. In the representatively shown arrangement, the outer shell member is a film composed of a low density polyethylene blend.

In a particular aspect of the invention, the shell member 22 has at least one appointed shell folding line 48, which in the representative configuration, is shown extending generally along the lateral dimension 88 of the article. Desirably, the shell fold line 48 has a location which corresponds to and substantially coincides with a location of at least one of the fold lines of the drape layer 28, such as laterally extending fold line 38 or 40. Accordingly, the shell member 22 and the drape layer 28 can be cooperatively, and if desired, simultaneously folded about their respective, coinciding lateral fold lines.

In particular aspects of the invention, the material of the shell portion 22 is configured to be substantially liquid impermeable. For example, the shell portion can be constructed of a substantially liquid impermeable polymer film. Alternatively, the shell portion can be composed of a fabric which has been treated or otherwise configured to be substantially liquid impermeable. For example, the shell portion may be composed of a sheet comprising a laminate of a polymer film and a woven or nonwoven fabric layer.

In other aspects of the invention, the material of the shell portion 22 is configured to be thermally fusible. For example the shell portion can include films or fibers which are heat-bondable. Accordingly, a bonding of the shell portion can be accomplished by adhesive bonding, thermal bonding, thermal-mechanical embossing or crimping, ultrasonic bonding, or the like.

The shell portion may also be configured to exhibit an increased coefficient of friction to help reduce slippage or other movement of the composite article relative to its underlying support surface. Various types of techniques may be employed to adjust the frictional coefficient. For example, the coefficient of friction can be increased by embossing the outer surface of the shell portion, applying a high-friction surface treatment, applying adhesives, employing blooming slip agents, coatings, applying chemical/electrical discharge treatments, or the like.

In a particular aspect of the invention, the outer shell portion 22 can have a fully open shell width 26 which is not less than about 10 centimeters (cm). Alternatively, the fully open shell width can be not less than about 15 cm, and optionally, can be not less than about 19 cm. In other aspects, the fully open shell width can be not more than about 53 cm. Alternatively, the fully open shell width can be not more than about 25 cm, and optionally, can be not more than about 21 cm to provide more efficient packaging for infant care components, such as disposable diapers.

The outer shell portion 22 can also have a fully open shell length 24 which is not less than about 20 cm. Alternatively, the fully open shell length can be not less than about 40 cm, and optionally, can be not less than about 50 cm. In other aspects, the fully open shell length can be not more than about 90 cm. Alternatively, the fully open shell length can be not more than about 80 cm, and optionally, can be not more than about 70 cm to provide a convenient packaging of the composite article 20.

In another aspect of the invention, the outer shell portion 22 can have a completely folded width 92 which is not less than about 10 cm. Alternatively, the completely folded shell width can be not less than about 15 cm, and optionally, can be not less than about 19 cm. In other aspects, the completely folded shell width can be not more than about 30 cm. Alternatively, the completely folded shell width can be not more than about 25 cm, and optionally, can be not more than about 21 cm to provide a convenient closed-package width of the composite article 20.

The outer shell portion 22 can also have a completely folded shell length 94 which is not less than about 15 cm. Alternatively, the completely folded shell length can be not less than about 17 cm, and optionally, can be not less than about 20 cm. In other aspects, the completely folded shell length can be not more than about 35 cm. Alternatively, the completely folded shell length can be not more than about 32 cm, and optionally, can be not more than about 30 cm to provide a convenient closed-package length of the composite article 20.

As illustrated, the outer shell portion can form an effective envelope around the folded drape layer and any associated unit articles contained therein. Desired arrangements of the outer shell member 22 are dimensioned to form an efficient envelope about an infant care diaper and a folded drape layer.

In the various configurations of the invention, the drape layer may be composed of any operative sheet material which is sufficiently flexible and foldable, such as a woven fabric, a nonwoven fabric, a paper layer, a polymer film or the like, as well as combinations thereof. The drape layer may be a substantially unitary member composed of a single, unit sheet of material, or may be an assembly composed of a plurality of pieces joined and affixed along their edges to form a larger contiguous sheet. Suitable woven fabrics include, for example, fabrics of cotton, rayon, linen, as well as other natural or synthetic fibers, and the like. Suitable nonwoven fabrics include hydroentangled pulp, spunbond fabrics, SMS (spunbond-meltblown-spunbond) fabrics, SBL (stretch-bonded-laminate) fabrics, GORTEX fabrics, STL (stretch-thermal-laminate) fabrics or the like, as well as combinations thereof. Suitable polymer films include films composed of polyethylene, LDPE (low-density polyethylene), LLDPE (linear low-density polyethylene), ULDPE (ultra-low-density polyethylene), HDPE (high-density polyethylene), polypropylene, polyethylene/EVA (ethylene vinyl acetate) copolymers, a blend of polyethylenes, paper, nylon, cellophane, PVC (polyvinyl chloride) film, metallic foil, metalized films, polyester films, microporous, breathable films or the like, as well as combinations thereof. The drape layer may also be configured to exhibit an increased coefficient of friction to help reduce slippage or other movement of the drape layer relative to its underlying support surface. The techniques employed to increase the coefficient of friction of the outer shell portion 22 may also be employed to increase the coefficient of friction of the drape layer 28.

As illustrated in FIG. 2A, for example, the drape layer 28 may include a nonwoven fabric layer portion 54 laminated to a barrier layer portion 56. The fabric portion is suitably joined and secured to the barrier portion with a suitable attachment mechanism, such as adhesive bonding, thermal bonding, sonic bonding, stitching, pinning, stapling, clipping, entangling, another system of chemical or mechanical interaction or the like, as well as combinations thereof. In a desired configuration, the drape layer 28 includes a nonwoven fabric portion composed of a polypropylene spunbond fabric provided at a basis weight of about 17 gsm (g/m$^2$). The fabric portion is laminated to a 3-layer barrier film portion, which has a total film thickness of about 0.0004 inch (about 0.01 mm) and is formed from a polypropylene catalloy resin.

In particular aspects of the invention, the drape layer 28 can be configured to be substantially liquid impermeable. For example, the drape layer can include a substantially liquid impermeable polymer film. In other arrangements, the drape layer can include a woven or nonwoven fabric which is water repellent, or has been treated or otherwise configured to be substantially liquid impermeable. For example, a woven or nonwoven fabric can be coated or otherwise treated with a water repellent material to impart an operative level of liquid impermeability. In a desired configuration, the drape layer 28 can be a laminate member composed of a nonwoven, spunbond polypropylene fibrous layer and a polypropylene catalloy barrier film.

At least a portion of the flexible drape layer 28 is affixed to the shell portion 22, and more particularly, the drape layer may be at least partially overlapped or otherwise superposed on the outer shell portion. In the shown arrangement, the drape layer 28 is superposed over substantially the entire outer shell portion 22.

With reference to FIGS. 1 and 2, the representatively shown configurations of the drape layer 28 include first and second longitudinal fold lines 34 and 36, which effectively delimit or divide the open drape width 32 into two or more, laterally adjacent, segments or sections. In particular arrangements, the longitudinal fold lines can provide for three, laterally adjacent segments. It should be readily apparent that the additional longitudinal fold lines may optionally be incorporated to divide the total drape width into further segments. In desired configurations, the number of longitudinal fold lines can be up to about 5 or more. Alternatively, the number of longitudinal fold lines is not more than 4, and optionally is not more than 2. In the various arrangements, the resultant width-wise segments of the drape layer can be unequal or substantially equal in width, as desired.

Similarly, the first and second lateral fold lines 38 and 40 can effectively delimit or divide the open drape length 30 into two or more, longitudinally adjacent sections or segments. In particular arrangements, the lateral fold lines can provide for three longitudinally adjacent sections. It should be readily appreciated, however, that the additional lateral fold lines may optionally be incorporated to delimit further lengthwise sections of the total drape layer. Desirably, the number of lateral fold lines can be up to about 4 or more, and optionally, is not more than 2. In the various arrangements, the resultant length-wise sections of the drape layer can be unequal or substantially equal in length, as desired.

In particular aspects of the various configurations of the invention, the drape layer can have a fully open drape width which is not less than about 32 cm. Alternatively, the fully open drape width can be not less than about 40 cm, and optionally, can be not less than about 44 cm. In other aspects, the fully open drape width can be not more than about 90 cm. Alternatively, the fully open drape width can be not more than about 50 cm, and optionally, can be not more than about 46 cm.

In other aspects of the various configurations of the invention, the drape layer 28 can provide a fully open drape length which is not less than about 35 cm. Alternatively, the fully open drape length can be not less than about 50 cm, and optionally, can be not less than about 62 cm. In other aspects, the fully open drape length can be not more than about 88 cm. Alternatively, the fully open drape length can be not more than about 80 cm, and optionally, can be not more than about 75 cm.

In a further aspect of the invention, the drape layer 28 can have a completely folded drape width 62 which is not less than about 8 cm. Alternatively, the completely folded drape width can be not less than about 10 cm, and optionally, can be not less than about 13 cm. In other aspects, the completely folded drape width can be not more than about 30 cm. Alternatively, the completely folded drape width can be not more than about 20 cm, and optionally, can be not more than about 16 cm.

In another aspect of the invention, the drape layer 28 can have a completely folded drape length 60 which is not less than about 10 cm. Alternatively, the completely folded drape length can be not less than about 14, and optionally, can be not less than about 20 cm. In other aspects, the completely folded drape length can be not more than about 35 cm. Alternatively, the completely folded drape length can be not more than about 30 cm, and optionally, can be not more than about 27 cm.

Various types of unit components 42 and/or 50 can be incorporated into the composite article of the invention. For example, the unit component can include a child's training pant, an adult incontinence product, a feminine care product, an item for changing automobile oil, an item for jewelry cleaning, an item for medical treatment, an item for first-aid, an item for gun cleaning, an item for shoe polishing, an item items for use at the beach, or the like.

In the representatively shown arrangements, a first unit component 42 can comprise a disposable absorbent article, such as the shown disposable diaper. The disposable diaper can have any conventional diaper configuration. For example, suitable disposable diapers are described in U.S. Pat. No. 5,192,606 entitled ABSORBENT ARTICLE HAVING A LINER WHICH EXHIBITS IMPROVED SOFTNESS AND DRYNESS AND PROVIDES FOR RAPID UPTAKE OF LIQUID, which issued Mar. 9, 1993 to D. Proxmire et al, the entire disclosure of which are incorporated by reference in a manner that is consistent herewith. Other suitable diapers are commercially available under the HUGGIES trademark.

The one or more unit components can be positioned onto a selected region of the open drape layer 28. In the arrangement representatively shown in FIG. 10, for example the unit component is positioned in a marginal end region of the drape layer 28 and is generally adjacent a terminal top edge of the drape layer. Optionally, the unit component may be positioned in a marginal side region generally adjacent a terminal side edge of the drape layer. In still other arrangements, such as representatively shown in FIG. 1, the first unit component 42 may be incorporated into the composite article 20 at a location which can be generally, centrally located within the area of the unfolded and laid-open drape layer 28. In particular, the first unit component 42 can be generally laterally-centralized, and located between the first and second longitudinal fold lines 34 and 36, respectively. Accordingly, at least one or more longitudinal fold lines may be interposed between the first unit component and each of the laterally opposed, terminal side edges of the drape layer. Additionally, the first unit component can be generally longitudinally-centralized, and positioned in between the first and second lateral fold lines 38 and 40, respectively. Accordingly, at least one or more lateral fold lines may be interposed between the first unit component and each of the longitudinally opposed, terminal end edges of the drape layer.

The drape layer member 28 has an appointed outward surface 64 and an oppositely positioned inward surface 66.

The outward surface 64 is appointed for positioning immediately adjacent the outer shell member 22. Desirably, the inward surface 66 is appointed to be a user side surface of the drape layer 28. In the shown configuration, for example, the outward surface 64 is provided by the barrier portion 56 of the drape layer, and the inward surface 66 is provided by the fabric portion 54 of the drape layer.

Accordingly, the first unit component 42 is removably positioned onto the fabric portion 54 of the drape member.

In particular aspects of the invention, the composite article 20 can include a second unit component, such as a toy, a pillow, a disposal bag, a packet 50 or the like, as well as combinations thereof. The packet may, for example, contain wet wipes, towelettes, lotions or creams. As representatively shown, the second unit component can comprise a separate packet which is composed of a substantially liquid impermeable material. The packet 50 is suitably constructed to operably enclose a selected plurality of wet wipes, and to retain the associated moistening liquid therein with the individual wipes. The packet desirably contains two or more wet wipes, and can optionally contain four or more wet wipes. In particular configurations, the packet 50 includes an operative packet opening system for selectively providing an access into the packet for removing the individual wipes from the packet for use, as desired. For example, the opening system can include a removable panel which can be selectively peeled away to expose an opening into the packet. Various types of conventional packet configurations can be employed with the present invention. Examples of suitable packet designs and opening systems can include a packet with a ZIPLOC opening, a hardpack with a latch opening, a pouch having a cover closed with a resealable adhesive, a packet with a frangible seal, or the like.

The individual wipes may also have various conventional configurations. For example, suitable wipes are of the type which are distributed under the brand name of HUGGIES Baby Wipes or COTTONELLE Personal Hygiene Wipes. Other suitable wipes can be of the type distributed under the brand name SCOTT Baby Fresh.

In a particular aspect of the invention, the second unit component, such as provided by wipes packet 50, is removably attached to a surface of the drape layer 28. For example, the shown configuration has the packet 50 attached to the inward surface 66 of the drape layer. More particularly, the packet 50 can be arranged to overlie and be immediately adjacent to the fabric portion 54 of the drape layer 28.

As illustrated by the representatively shown arrangements, the packet 50 may be positioned in an underlying or overlying, superposed relation at substantially the same location as the first unit component. Thus, the packet may be located in a generally central section of the drape layer. The packet may alternatively be positioned in a marginal end or side region of the drape layer 28. As illustrated by the arrangement shown in FIGS. 2 and 3, for example, the packet 50 can be located generally adjacent a terminal edge of the drape layer, and optionally may be constructed to be selectively pivotable from its storage position (FIG. 3), which is located inboard of the terminal edge, to its active, working position (FIG. 2), which is located outboard of the terminal drape edge.

More particularly, the packet 50 can be pivotably attached to either the inner or outer surface of the drape layer 28 at a location which is generally adjacent to a terminal edge 58 of the drape layer. In the representatively shown arrangement, the packet 50 is pivotably movable to an active location which is relatively outboard of the terminal edge 58 of the drape layer, as determined when the drape layer 28 is in its unfolded condition. As representatively shown, the packet 50 can include a readily flexible and bendable edge region which is pivotably attached to the drape layer 28 and/or to an inward surface of the shell member 22. As a result, the packet is pivotably movable to thereby transition the packet from its first, storage position to its second, active position. The resultant configuration can allow the wipes packet 50 to be flipped away from the drape member 28. The configuration can hold the packet in place during a one-handed removal of wipes, and can also prevent the packet from falling onto the floor.

In another aspect of the invention, the packet opening mechanism 52 of the packet 50 can be selectively arranged for an efficient presentation into a convenient use position. Desirably, when the packet 50 is pivoted from its storage position to its active position, the resultant movement thereby transitions the packet opening mechanism 52 from a first storage position to a second active position. The first storage position has the opening mechanism 52 facing toward and positioned immediately adjacent to the appointed inward surface 66 of the drape layer 28. The second active position has the packet opening mechanism 52 facing away from and generally in the same direction as the inward surface of the drape layer. Where the opening mechanism includes a pull-tab 53 for initiating the opening process, the pull-tab is desirably located along a laterally extending edge of the opening mechanism which is relatively closer to the terminal edge 58 of the drape layer. The pull-tab can be located at an inboard edge of said packet opening mechanism, as determined after the packet 50 has been pivoted or otherwise moved to its second, active position. As a result, when the packet 50 is deployed to its active position and an object, such as an infant, is placed onto the drape layer, the weight of the object can hold in place the drape layer and the attached packet 50 during the pulling of the tab 53 to open the packet. Thus, the opening of the packet can be accomplished with a single hand.

In the shown arrangements, the packet 50 is pivotable about a pivot axis 70 which extends generally within or parallel to a plane of the drape layer 28 when the drape layer is in its unfolded condition. In addition, the pivot axis can be substantially parallel to the bottom, terminal edge 58 of the drape layer.

In an optional aspect of the invention, the packet 50 can be releasably attached to the drape layer 28. The releasability can, for example, be provided by a frangible bond between the packet and the drape layer. The frangible bond can, for example, be provided by an appointed region of frangibility, a releasable adhesive fastener, a releasable mechanical fastener, or the like. Examples of releasable mechanical fasteners include snaps, zippers, ZIPLOC fasteners, cooperating hook-and-loop fasteners (including, e.g. mushroom-and-loop fasteners), clips, other cooperating systems of interengaging mechanical elements, or the like, as well as combinations thereof.

In the shown configuration, the packet opening mechanism 52 can include a line or other suitable region of frangibility. Alternatively, the packet opening mechanism 52 can include a removable cover piece which is releasably secured to the packet with a releasable seal. The cover piece may include a grasping pull-tab, and may or may not be completely detachable from the packet. The releasable seal can, for example, be provided by a releasable adhesive, or a releasable mechanical fastener, such as described elsewhere herein.

Figure 3:
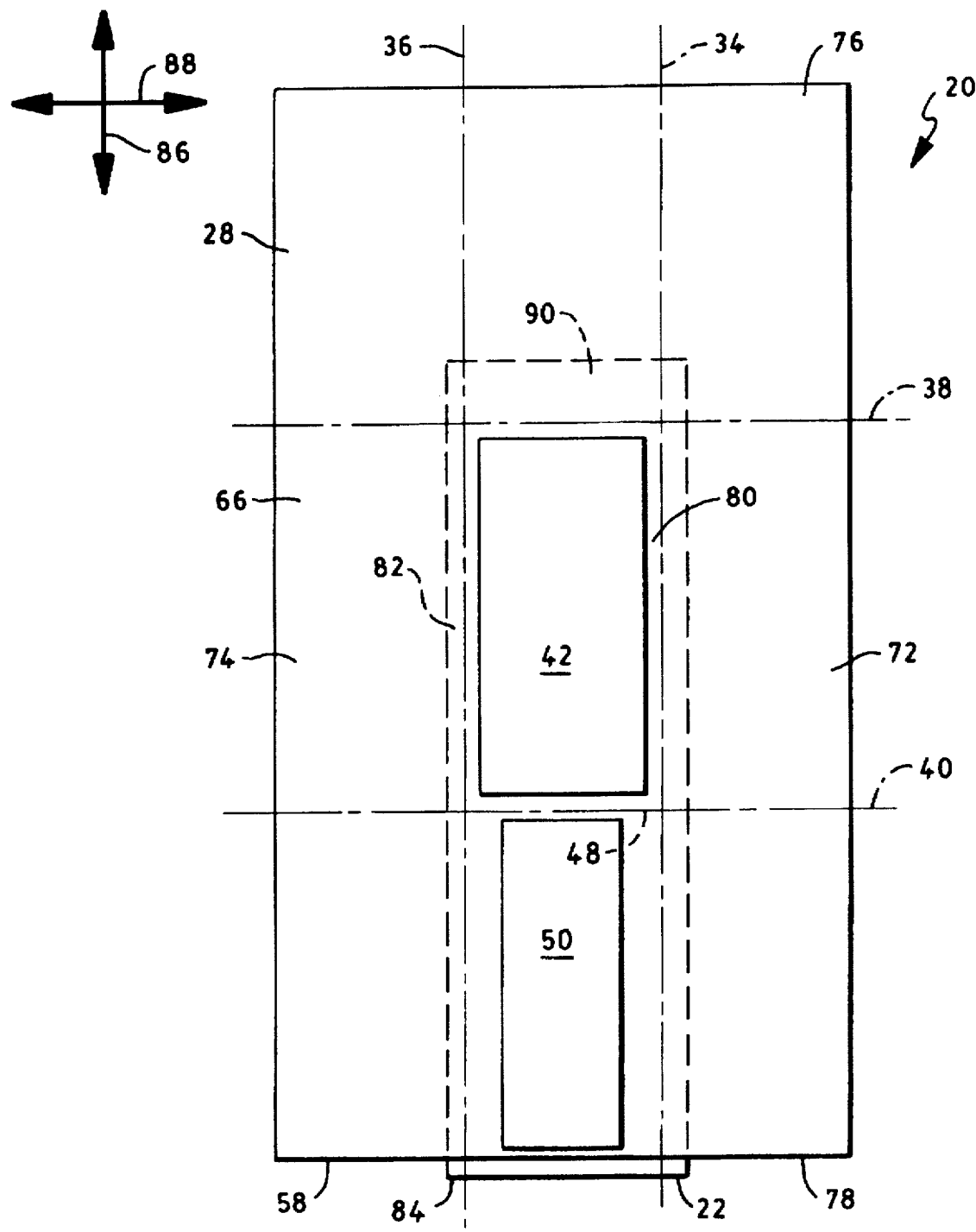
FIG. 3 representatively shows an article of FIG. 2 in which a packet has been moved from its working position to a storage position.

The composite article of the invention can advantageously be folded and configured into an efficient, compact, package condition. With reference to FIGS. 2 and 3, the second unit component 50, if incorporated, is positioned in its storage position overlying the inward surface 66 of the drape layer 28. With reference to FIGS. 4 through 8, the composite article of FIG. 2 is further folded to provide a closed-package configuration of the composite article 20. It should be readily apparent, however, that the sequences and operations shown and described in FIGS. 4 through 8 would also be equivalently or similarly applicable to the composite article configuration which is representatively shown in FIG. 1.

Figure 4:
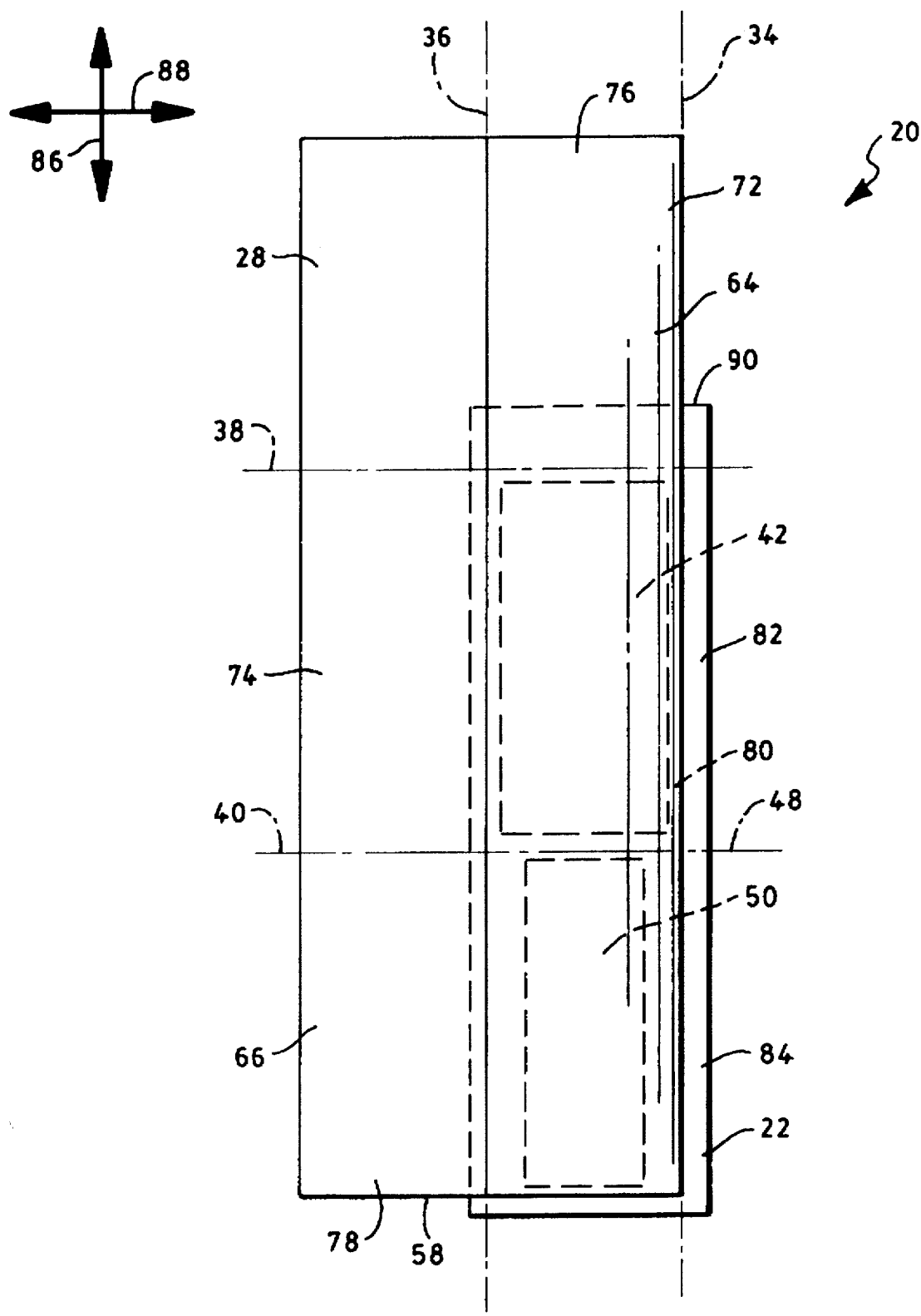
FIG. 4 representatively shows an article of FIG. 3 in a partially folded and partially closed condition.
Figures 5, 5A:
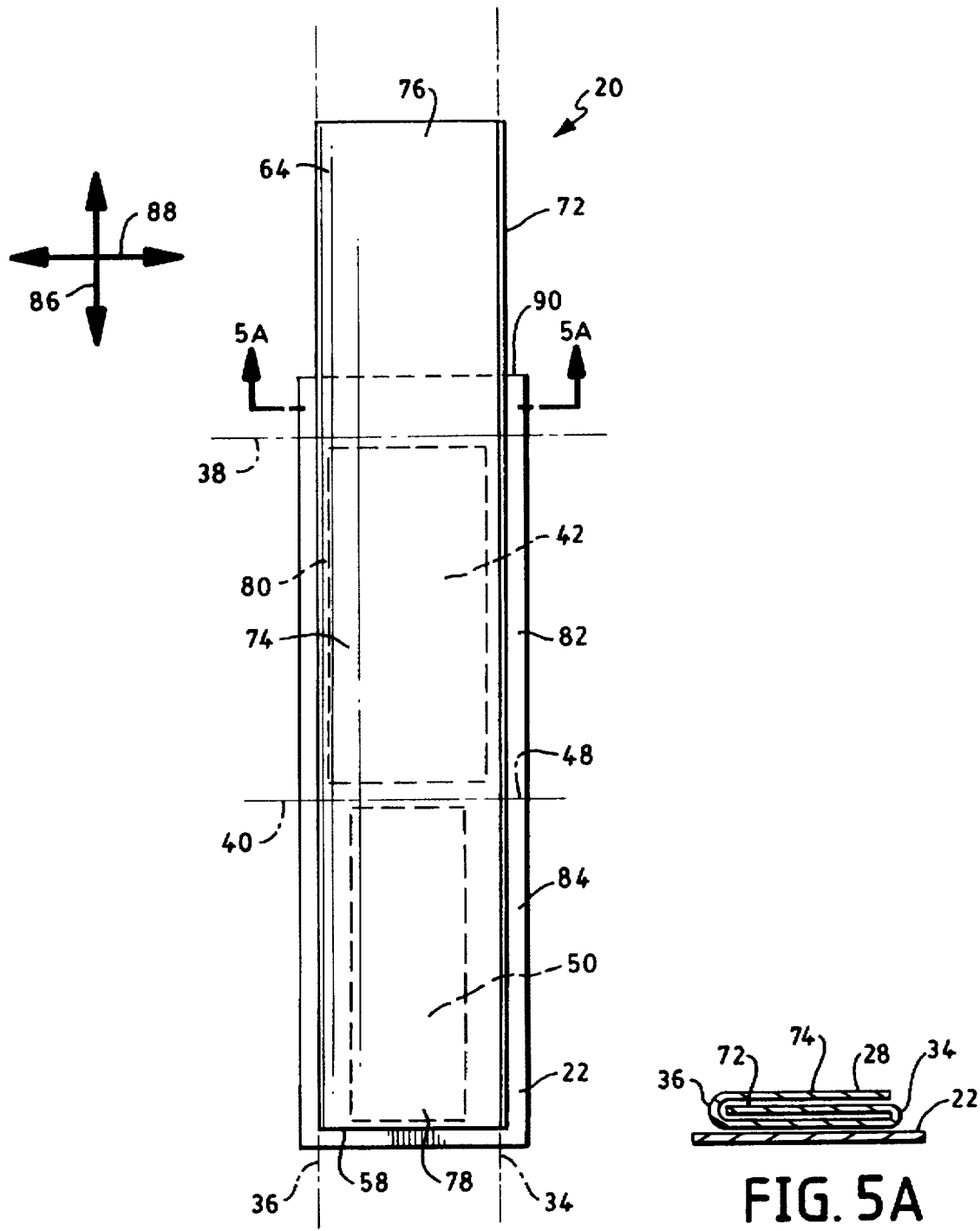
FIG. 5 representatively shows an article of FIG. 4 in a further partially folded and partially closed condition.
FIG. 5A shows a cross-sectional view of the article in FIG. 5, taken at line 5A—5A.

With reference to FIGS. 4 and 5, the drape layer member can be folded along its first and second longitudinal fold lines 34 and 36, respectively, in any suitable sequence. In the shown arrangement of FIG. 4, for example, a first side section 72 at the right-side of the drape layer 28 is moved laterally towards the left about the first longitudinal fold line 34 to overlie the inward surface 66 of the drape layer and to overlie the first unit component 42, and to overlie the second unit component, if incorporated into the composite article. A second side section 74 at the left-side of the drape layer 28 can then be laterally moved to the right to be folded about the second longitudinal fold line 36 to overlie the first side section 72 of the drape layer, as illustrated in FIG. 5. Accordingly, the inward surface of the second side section 74 overlies immediately adjacent to the outward surface of the first side section 72.

Figure 6:
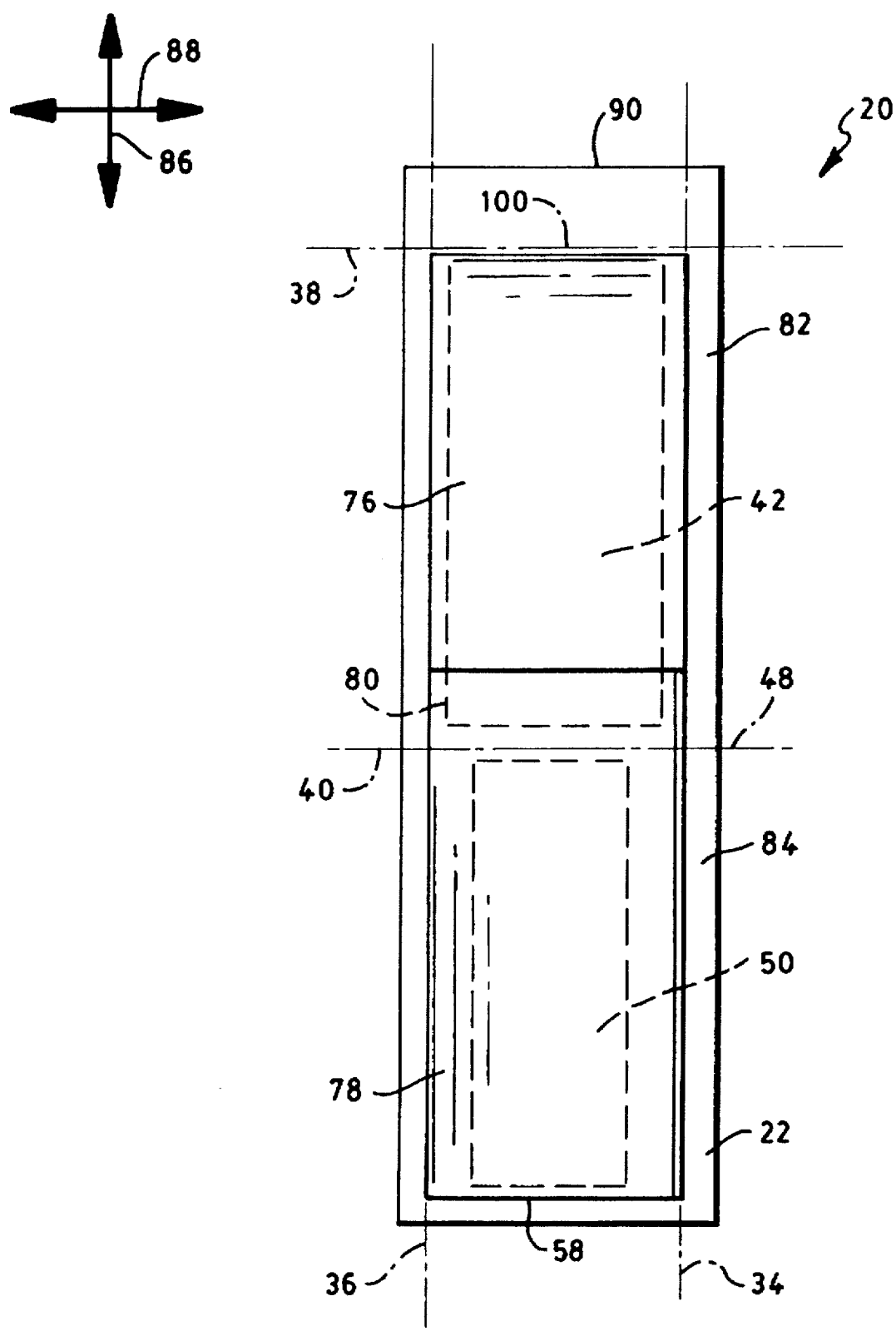
FIG. 6 representatively shows an article of FIG. 5 in a further partially folded and partially closed condition.

With reference to FIG. 6, a first end section 76 at the top-end of the drape layer can be moved longitudinally downward to fold about the first lateral fold line 38 to overlie the central section 80 of the drape layer, and to overlie the first unit component 42. Additionally, with reference to FIG. 7, a second end section 78 at the bottom-end of the drape layer can be moved generally longitudinally upward to fold about the second lateral fold line 40 to overlie the central section 80 of the drape layer and to overlie the folded-over first end section 76. Accordingly, the drape layer 28 has a fully folded length 60 and a fully folded width 62.

In the shown configuration, the second lateral fold line 40 of the drape layer generally coincides with the shell fold line 48, and the shell fold line generally delimits a first section 82 of the shell member 22 and a second section 84 of the shell member. The first shell section 82 may be separate from or releasable from the drape layer 28. Similarly, the shell second section 84 may be separate from or releasable from the drape layer 28. In the illustrated arrangement, at least the first shell section 82 is substantially affixed to the outward surface 64 of an immediately adjacent section of the drape layer 28. Optionally, the first and second shell sections can both be affixed to the appointed outward surface of the drape layer. Accordingly, the longitudinally upward folding of the second end section 78 of the drape layer about its second lateral fold line 40 can simultaneously carry the second section 84 of the shell member 22 to fold about its selected fold line 48.

In its various arrangements, the second shell section 84 can be moved to fold about the shell fold line 48 to overlie onto the folded drape layer, as representatively shown in FIG. 8.

Figure 9:
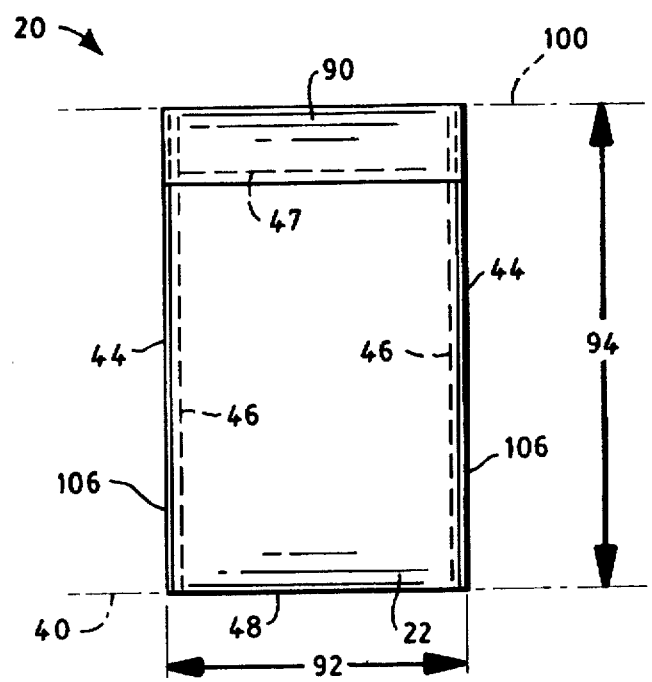
FIG. 9 representatively shows an article of the invention in its completely folded and closed condition.

Desirably, the shell member 22 can provide for a third foldable section which provides for a closure flap 90, as representatively shown in FIGS. 8 and 9. The closure flap can be moved to fold about a closure fold line 100 to envelope its associated, closely adjacent end edge region of the folded drape layer 28, and operatively affixed to an exposed surface of the shell member 22 to provide for the desired closed-package condition. For example, the closure flap 90 can be configured to overlie and be secured to a cooperating contacting surface portion of the shell member 22 with any of the attaching or closure mechanisms described herein.

In particular aspects of the invention, the shell member 22 has a folded width 92 which is greater than the folded width 62 of the drape layer 28. Additionally, the shell member 22 can have a folded length 94 which is greater than the folded length 60 of the drape layer. Accordingly, the shell member 22 can provide an outer layer which substantially envelopes the folded drape layer and the associated unit components, such as the diaper and the packet 50.

With reference to FIGS. 8 and 9, a suitable closure mechanism 44 holds the shell member portion 22 in a closed-package condition. Suitable closure mechanisms can, for example, include adhesive bonds, thermal bonds, sonic bonds, thermal-mechanical embossing, crimping, zippers, ZIPLOC fasteners, hook-and-loop fasteners, stitching, pins, staples, clips or the like, as well as combinations thereof. In the illustrated arrangement, a pattern of thermal-mechanical bonds are distributed along the initially open, unattached edges of the shell member 22 to operably close the edge regions and provide the desired closed-package condition. In an optional configuration, the closure mechanism, such as provided by a lineal array of interlocking thermal-mechanical embossments, can extend along one open end edge region and along a pair of laterally opposed side edge regions of the folded shell member 22 to thereby close and seal the composite article 20 in its packaged condition.

In desired aspects of the invention, the composite article 20 can include an article opening mechanism which allows a selective defeating of the closure mechanism 44 to provide a convenient access to the drape layer 28 and its associated unit components. For example, the article opening mechanism can include a system of frangible lines 46 which are positioned adjacent to and relatively inboard from the attachments employed to generate the closure mechanism 44. Alternatively, the article opening mechanism can be provided for by a closure mechanism 44 which is selectively constructed and arranged to provide a readily frangible region or a releasable attachment along the corresponding interassembled edge regions of the closed shell member 22. For example, the opening mechanism can be provided for by a closure system/mechanism which includes an array of interlocking, thermal-mechanical embossments or other bonds which have been configured to be selectively releasable. Upon the application of a predetermined amount of opening force, the bonds or interlocked embossments can be separated while substantially avoiding an excessive tearing of the shell member material.

In the arrangement which incorporates the closure flap 90, a closure flap attachment 47 can be configured to be selectively separable to allow a movement of the closure flap to its open, substantially unfolded condition. In the illustrated arrangement, for example, the closure flap attachment is provided by an adhesive which can be selectively released or otherwise unfastened, and the released edge of the shell member 22 can be grasped and pulled to operably detach and separate the frangible regions to allow an opening and unfolding of the previously closed shell member 22. Examples of other releasable attachments include zippers, ZIPLOC fasteners, hook-and-loop fasteners, releasable stitching or the like, as well as combinations thereof.

In particular configurations where the closure flap 90 includes a closure flap attachment 47 provided by a releasable and refastenable adhesive, at least a portion of the adhesive can be selectively constructed to substantially separate away from the flap 90 and remain operatively attached to an exposed, outerside surface of the shell member 22. For example, with reference to FIG. 8, a major portion of the releasable adhesive could be constructed to remain attached to the non-flap portion of the shell member 22. With reference to FIG. 16, a major portion of the releasable adhesive could optionally be constructed to remain attached to an appointed outside surface of the flap portion of the shell member 22. Thusly configured, when the closure flap is opened and the shell member is unfolded to access the drape layer, an operably sufficient portion of the adhesive can be available on the outer surface of the shell member for releasably bonding to a table or other immediately contacting surface to thereby reduce slippage between the surface and the opened composite article 20.

When the selected opening mechanism is activated, the drape layer 28 can be unfolded to its open, user position. The unit components, such as the diaper and the wipes packet 50, can then be readily accessed and used. The unfolding of the drape layer 28 and the movement or removal of the contained unit components can occur in a sequence which is substantially a reverse of the sequence which was employed to enclose the unit components, and to fold the drape layer 28 and outer shell member 22.

Figure 10:
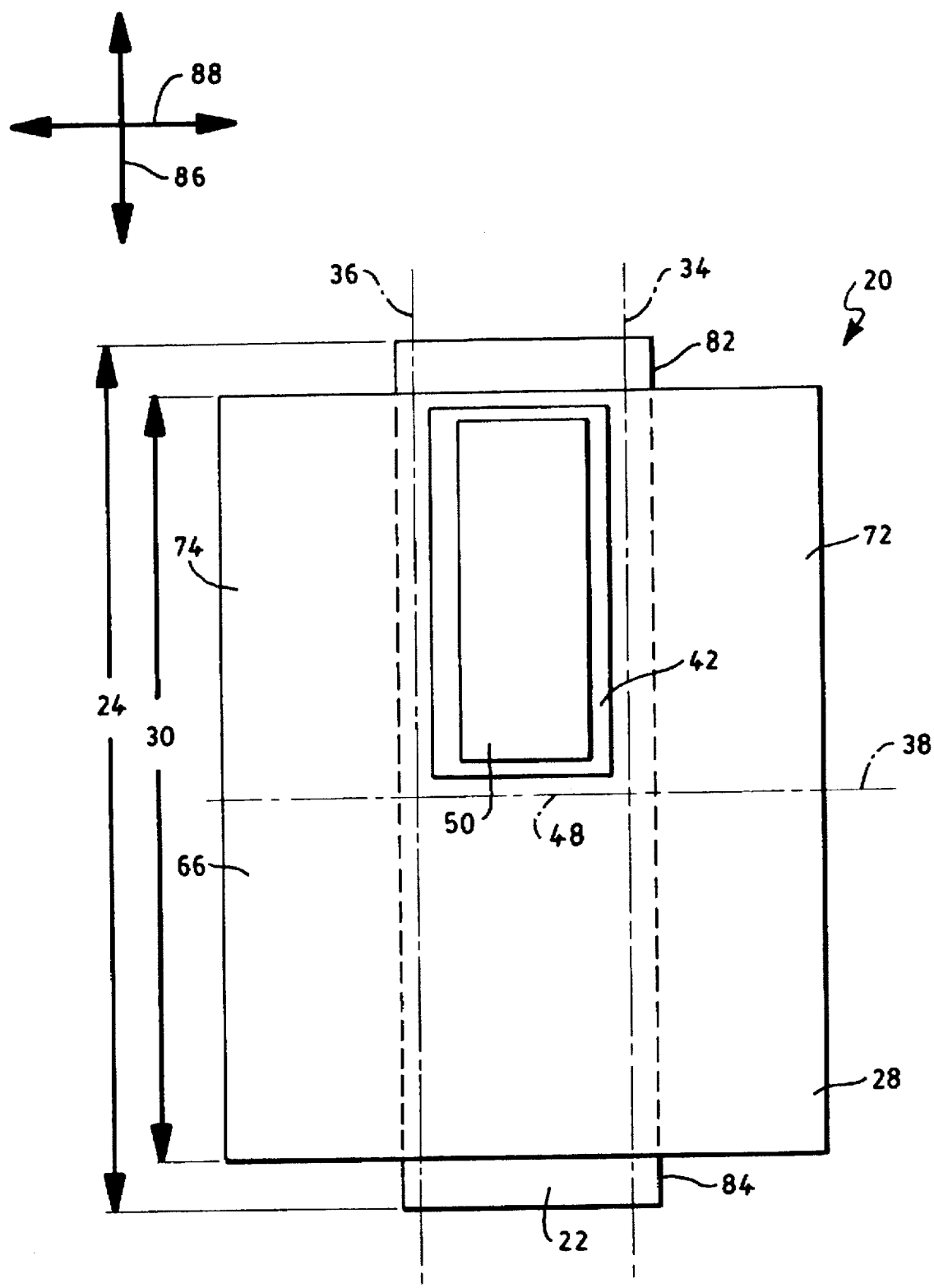
FIG. 10 representatively shows an article of the invention having a single lateral fold line and a multiplicity of longitudinal fold lines.

With reference to FIGS. 10, 11 and 12, the composite article 20 may include a drape layer 28 having a single laterally extending fold line 38 and a multiplicity of longitudinally extending fold lines. The drape layer in FIG. 10 has a pair of longitudinal fold lines 34 and 36, and the outer shell member 22 is substantially centered with respect to the lateral dimension 88 of the drape layer. In addition, the drape layer has an open length 30 which is less than the open length 24 of the outer shell 22. The drape layer in FIG. 11 has three longitudinal fold lines 34, 35 and 36, and the outer shell member 22 is asymmetrically positioned with respect to the lateral dimension of the drape layer. The drape layer in FIG. 12 has four longitudinal fold lines 34, 35, 36 and 37, and the outer shell member 22 is again substantially symmetrically positioned with respect to the lateral dimension of the drape layer.

In the shown configurations, the location of the lateral fold line 38 generally corresponds to the location of the shell fold line 48. The outer shell portion 22 may be substantially centered with respect to the width of the drape layer 28 (e.g. FIG. 10), or may be asymmetrically offset towards one side of the drape layer, when the drape is in its fully opened, unfolded condition (e.g. FIG. 11). Similarly, the initial location of any or all of the unit components, such as the diaper 42 and packet 50, may be substantially centered with respect to the width of the drape layer 28, or may be asymmetrically offset towards one side of the drape layer, when the drape is in its fully opened, unfolded condition. The folds with respect to the longitudinal fold lines may all be arranged to turn or pivot in generally the same direction, or may be arranged to pivot in a zigzag, accordion-type configuration. In addition, the drape layer member may be folded along its longitudinal fold lines in any suitable sequence.

Figure 12B:
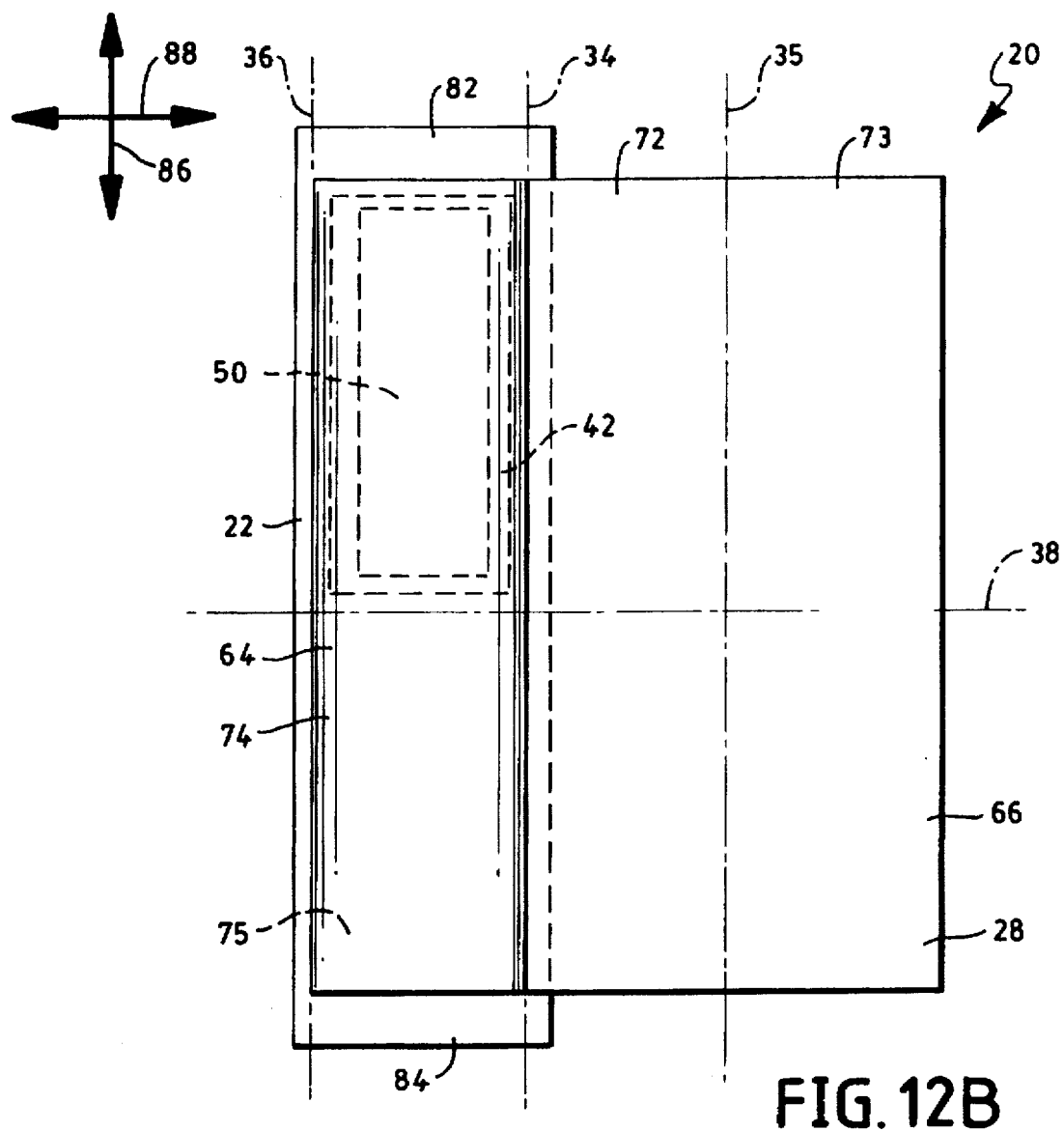
FIG. 12B representatively shows an article of FIG. 12A in a further partially folded and partially closed condition.
Figure 12C:
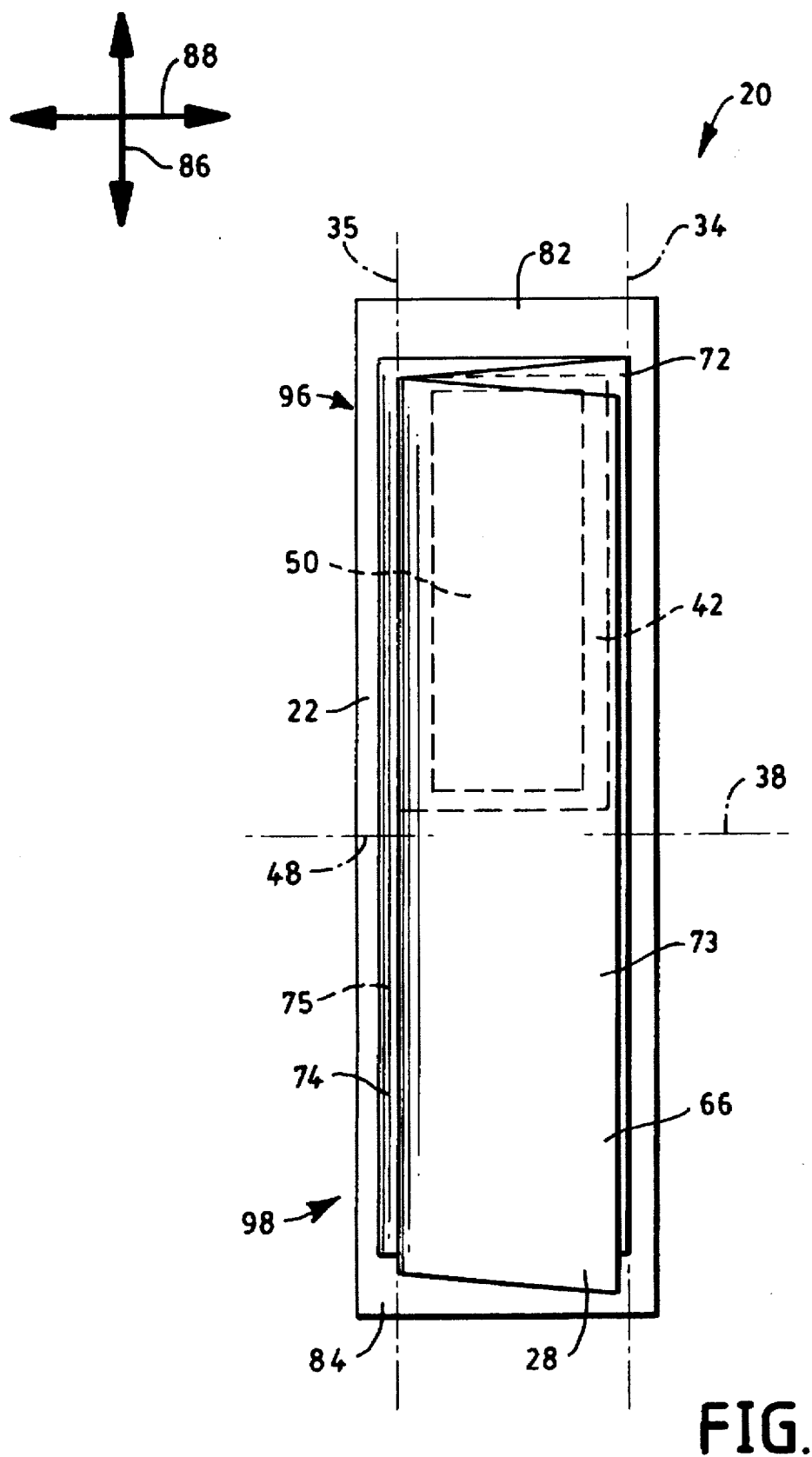
FIG. 12C representatively shows an article of FIG. 12B in a further partially folded and partially closed condition employing an accordion-type fold.

With reference to the arrangement shown in FIGS. 12A, for example, an initial side section 75 at the left-side of the drape layer 28 can be pivoted laterally towards the right about an initial longitudinal fold line 37 onto the side section 74 to overlie the inward surface 66 of the drape layer. With reference to FIG. 12B, the side sections 74 and 75 can together be pivoted about the longitudinal fold line 36 to again overlie the inward surface 66 of the drape layer. The side sections 74 and 75 also overlie the first unit component 42 and the second unit component, if incorporated into the composite article. With reference to FIG. 12C, the side section 72 and a further side section 73 may then be accordion-folded to overlie the previously folded, side sections 74 and 75. In should be readily appreciated that an operative combination of the folding operation described with respect to FIGS. 12A through 12C may also be employed to fold the initial drape layer configurations representatively shown in FIGS. 10 and 11.

Figure 12D:
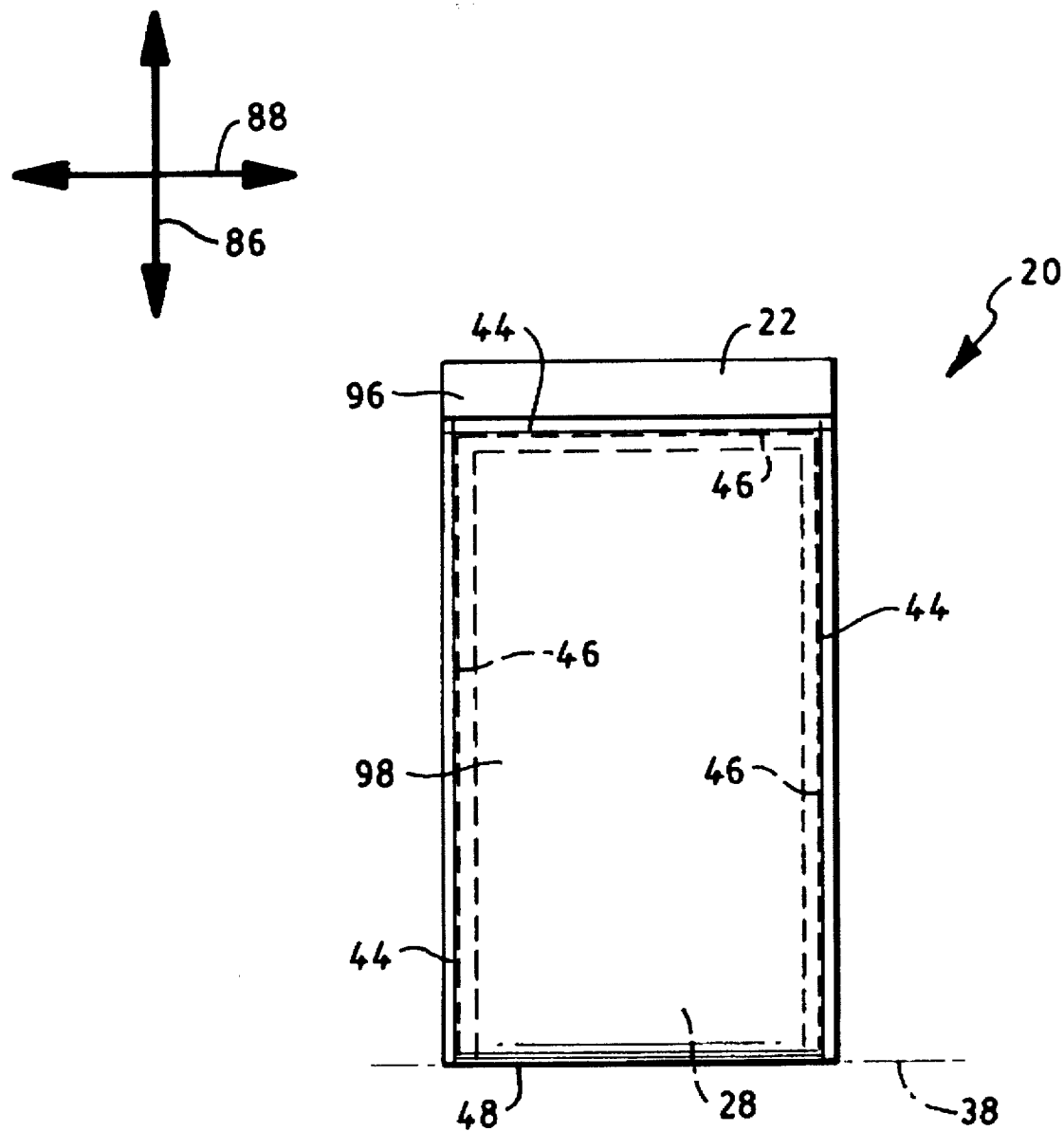
FIG. 12D representatively shows an article of FIG. 12C in its completely folded and closed condition.

As illustrated in FIG. 12C, the shown configuration of the laterally extending, drape layer fold line 38 generally coincides with the shell fold line 48 located between the first and second sections 82 and 84 of the shell member 22. The assembly has a top-end portion 96 and a bottom-end portion 98. In the illustrated arrangement, the first and second shell sections are both affixed to the appointed outward surface of the drape layer, although either or both of shell sections may be separate from or releasable from the drape layer 28. With reference to FIG. 12D, the resultant intermediate assembly of the composite article can then be further folded by pivoting the bottom-end portion 98 of the assembly about the lateral drape fold line 38 and the shell fold line 48 to overlie the top-end portion 96 of the assembly.

As previously described with respect to FIGS. 8 and 9, a suitable closure mechanism 44, such as adhesive or an array of interlocking thermal embossments, holds the shell member portion 22 in a closed-package condition. In addition, the shell member 22 may include a third foldable section which provides for a closure flap 90. In either arrangement, the shell member 22 provides a protective outer layer which substantially envelopes the folded drape layer and the associated unit components, such as the shown diaper and packet.

Also as previously described, the composite article 20 can include an article opening mechanism which allows a selective defeating of the closure mechanism 44 to provide a convenient access to the drape layer 28 and its associated unit components. For example, the article opening mechanism can include a system of frangible lines 46, or an array of interlocking, thermal-mechanical embossments which have been constructed to be selectively releasable. Upon the application of a predetermined amount of opening force, the interlocked embossments can separate while substantially avoiding a tearing of the shell member material. When the selected opening mechanism is activated, the drape layer 28 can be unfolded to its open, user position. The unit components, such as the diaper and the wipes packet 50, can then be readily accessed and used. The unfolding of the drape layer 28 and the movement or removal of the contained unit components can occur in a sequence which is substantially a reverse of the sequence which was employed to enclose the unit components and fold the drape layer 28 and outer shell member 22.

It should be readily appreciated that the composite article 20 may include decorative and/or informational graphics on the outer shell member 22, the drape layer 28, or other component of the composite article. In addition, the composite article 20 can further employ a displaying mechanism for presenting the composite article to user. For example, the displaying mechanism can comprise an edge region of the closed outer shell member 22 which has been perforated (e.g. FIG. 15). The perforation 102 allows a hanging of the composite article on a display hook or rod. The perforation may be located, and desirably centered, in a relatively shorter-length edge region of the shell member 22, or may be located in a relatively longer-length edge region of the shell member, as desired. Examples of other suitable displaying mechanisms can include hooks, tabs, straps, clips, pins, latches, adhesive strips or the like, as well as combinations thereof.

Particular aspects of the invention can be configured to provide a closure flap 90 in combination with a reinforced region along an edge of the closed-package condition of the composite article 20. For example, FIG. 13 representatively shows a partially folded composite article, which is disposed in a condition similar to that generated by the previously discussed, folding sequence, which was employed to produce the arrangement illustrated in FIG. 6. FIG. 13A shows a simplified schematic, length-wise cross-sectional view of the shell member 22, with the contained contents shown generally at 104. The details of the contents 104, such as the details of the partially folded drape layer and the enclosed unit components, have been omitted for the sake of clarity. The illustrated outer shell member 22 includes two laterally opposed, longitudinally extending side edge regions 106, a first end region 108 and a second end edge region 110. The first end region of the shell member includes a generally zig-zag or serpentine z-fold to provide the closure flap 90 and a multilayer reinforced edge region 112. The z-fold has a first, relatively outboard, folded edge line 114, and a second, relatively inboard, folded edge line 116. The reinforced region 112 can then include the desired perforation 102, with the multiple layers providing increased strength around the perforation.

Figure 15:
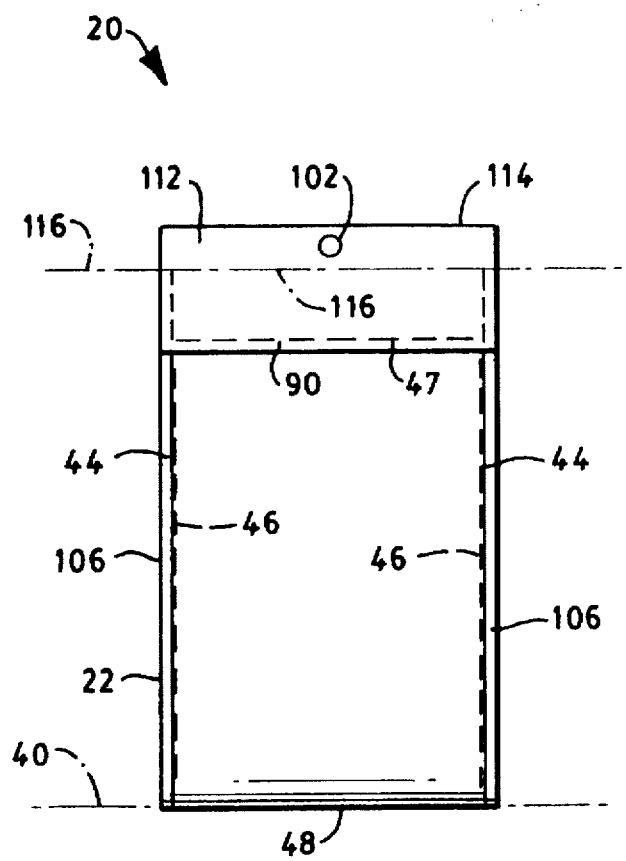
FIG. 15 representatively shows an article of FIG. 14 in a fully folded and closed condition.
Figure 15A:
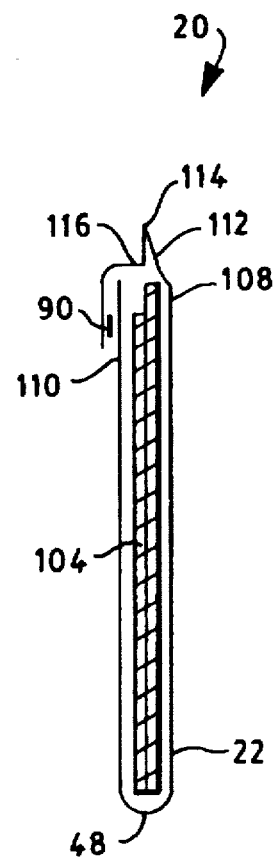
FIG. 15A representatively shows a simplified, schematic, cross-sectional view of the article of FIG. 15.

With reference to FIGS. 14 and 14A, the shell member 22 (and associated contents) can be folded and moved about the shell fold line 48 (and the second lateral fold line 40 of the drape layer 28) to bring the second end region 110 to a location which is generally adjacent to the first end region 108. With reference to FIGS. 15 and 15A, the closure flap 90 can then be pivoted about the inboard line 116 and moved down to a closed location which overlies the second end region 108. The closed flap is fastened to the second end region 108 with an attachment 47 that is operatively-defeatable by the system of the selected opening mechanism.

Figure 17:
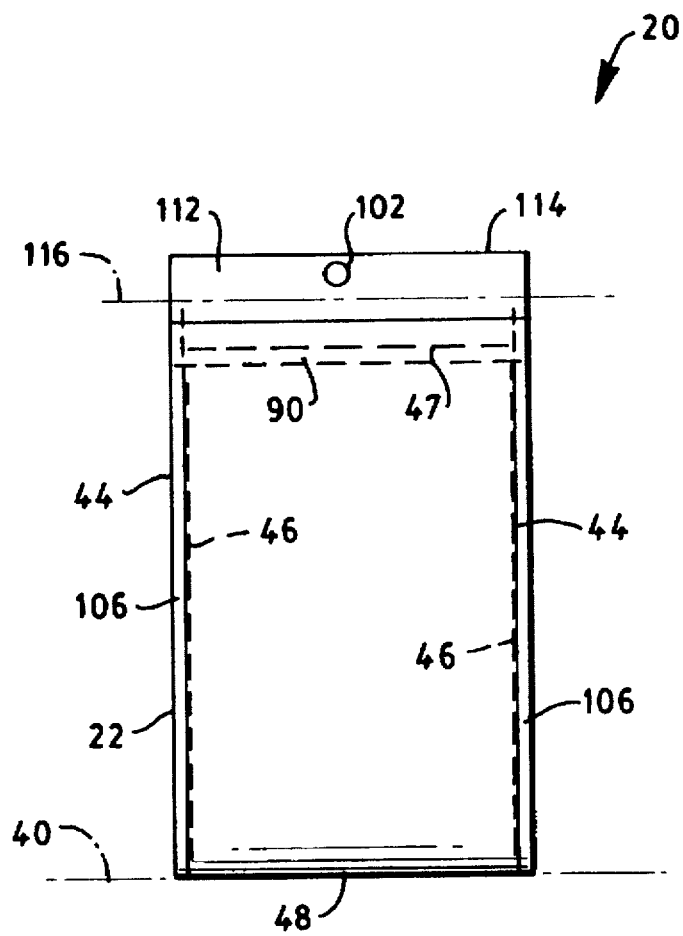
FIG. 17 representatively shows an article of FIG. 16 in its fully folded and closed condition.
Figure 17A:
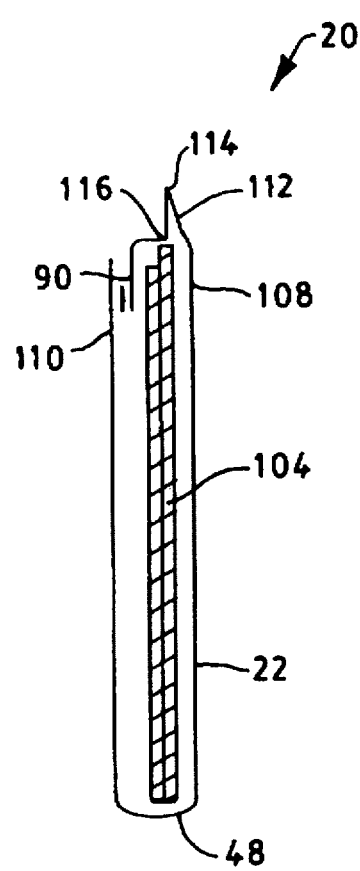
FIG. 17A representatively shows a simplified, schematic, cross-sectional view of the article of FIG. 17.

Another aspect of the invention is representatively shown with reference to FIGS. 13 and 13A, and FIGS. 16 through 17. As previously mentioned, FIG. 13 representatively shows a partially folded composite article, and FIG. 13A representatively shows a schematic, length-wise cross-sectional view of the shell member 22, with the contained contents shown generally at 104. With reference to FIG. 16 and 16A, the appointed closure flap 90 can be pivoted about the inboard line 116 and moved down to a closed location which overlies the contents 104. With reference to FIGS. 17 and 17A, the shell member 22 (and associated contents) can then be folded and moved about the shell fold line 48 (and the second lateral fold line 40 of the drape layer) to bring the second end region 110 to a location which overlies the closed position of the flap 90. The second end region 110 is fastened to the closed flap with an attachment 47 that is operatively-defeatable by the system of the selected opening mechanism.

In the various configurations of the invention, soiled items can be gathered up into the drape layer for convenient disposal. Where the closure flap attachment 47 provides for a refastenable mechanism, the closure mechanism for the flap may be constructed and arranged to operably attach to a suitably appointed landing zone to thereby hold the drape layer in its gathered-up condition around any soiled items contained in the drape layer.

For the purposes of the present description, the composite article and its associated unit components have been oriented as shown in the Figures, and particular directions have, for the sake of convenience, been designated as the length and width dimensions. It should be readily appreciated, however, that relative orientation of the composite article 20 and/or its associated components, whether in their folded or unfolded condition, can be rotated approximately 90 degrees in either direction, rotated approximately 180 degrees or rotated through some other intermediate angle to provide substantially equivalent structures. It should also be readily appreciated that any graphics employed on the outer surface of the outer shell portion may be oriented for intended display at any desired rotational angle of the composite article. For example, the intended display of the graphics may be when the longer dimension of the closed package is aligned horizontally, or optionally may be when the shorter dimension of the closed package is aligned horizontally.

Having described the invention in rather full detail, it will be readily apparent to a person of ordinary skill that various changes and modifications may be made without departing from the spirit of the invention. All of such changes and modifications are contemplated as being within the scope of the invention, as defined by the subjoined claims.

We claim:

1. A composite article having a longitudinal, length dimension and a lateral, width dimension, said article comprising:

a flexible outer shell portion having a shell length and a shell width;

a flexible drape layer, at least a portion of which is substantially affixed to said shell portion, said drape layer having a drape width which is larger than said shell width, a first laterally extending fold line, a first longitudinally extending fold line and at least a second longitudinally extending fold line, said longitudinally extending fold lines providing for a longitudinally-folded drape width which is not more than said shell width;

at least one unit component, which is contained and enveloped within said drape layer when said drape layer is folded;

a closure means for holding said shell portion in a closed-package condition which substantially envelops said drape layer when said drape layer is folded; and an article opening means for selectively defeating said closure means to provide access to said at least one unit component.

2. A composite article as recited in claim 1, wherein said drape layer further includes at least a second laterally extending fold line, and wherein said laterally extending fold lines provide for a laterally-folded drape length which is not more than said shell length.

3. A composite article as recited in claim 1, wherein said drape layer is affixed in a superposed relation to said shell portion.

4. A composite article as recited in claim 1, wherein said outer shell portion has at least one appointed shell fold line.

5. A composite article as recited in claim 4, wherein said shell fold line extends laterally and has a location which substantially coincides with a location of at least one of said laterally extending fold lines of said drape layer.

6. A composite article as recited in claim 1, wherein said shell portion is configured to be substantially liquid impermeable.

7. A composite article as recited in claim 1, wherein said shell portion is thermally fusible.

8. A composite article as recited in claim 1, wherein said drape layer is configured to be substantially liquid impermeable.

9. A composite article as recited in claim 8, wherein said drape layer includes a nonwoven fabric portion laminated to a barrier portion.

10. A composite article as recited in claim 1, wherein said at least one unit component comprises a disposable diaper.

11. A composite article as recited in claim 10, further comprising a second unit component which includes a plurality of wet wipes.

12. A composite article as recited in claim 11, wherein said wet wipes are enclosed in a separate, substantially liquid impermeable wipes packet.

13. A composite article as recited in claim 12, wherein said wipes packet includes a packet opening mechanism for selectively providing an access for removing said wipes from said wipes packet.

14. A composite article as recited in claim 12, wherein said drape layer includes a nonwoven fabric portion laminated to a barrier portion, and said wipes packet is attached to said drape layer to overlie onto said nonwoven fabric portion.

15. A composite article as recited in claim 12, wherein said wipes packet is pivotably attached to said drape layer adjacent a terminal edge of said drape layer, and said wipes packet is pivotably moveable to a location which is relatively outboard of said terminal edge of said drape layer when said drape layer is in its unfolded condition.

16. A composite article as recited in claim 13, wherein said wipes packet is pivotably attached to said drape layer, and said wipes packet is pivotably movable to thereby transition said packet opening mechanism from a first position to a second position, said first position facing toward said drape layer, and said second position facing away from said drape layer.

17. A composite article as recited in claim 16, wherein said packet opening mechanism includes a pull-tab located at an inboard edge of said packet opening mechanism, as determined after said packet has been moved to its second position.

18. A composite article as recited in claim 16, wherein said wipes packet is pivotable about a pivot axis which extends generally parallel with a plane of said drape layer when said drape layer is in its unfolded condition.

19. A composite article as recited in claim 13, wherein said wipes packet is releasably attached to said drape layer.

20. A composite article as recited in claim 1, wherein said outer shell portion includes a z-folded end region.

* * * * *